(12) United States Patent
Yoshimura

(10) Patent No.: US 6,619,839 B2
(45) Date of Patent: Sep. 16, 2003

(54) X-RAY OBJECT POSITIONING APPARATUS FOR USE IN X-RAY IMAGING APPARATUS AND X-RAY IMAGING APPARATUS PROVIDED WITH THE SAME

(75) Inventor: Takahiro Yoshimura, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 0 days.

(21) Appl. No.: 10/076,928

(22) Filed: Feb. 15, 2002

(65) Prior Publication Data
US 2002/0122537 A1 Sep. 5, 2002

(30) Foreign Application Priority Data

Feb. 16, 2001 (JP) ........................... 2001-040632
Aug. 21, 2001 (JP) ........................... 2001-250822

(51) Int. Cl.$^7$ .............................. A61B 6/14; H05G 1/02
(52) U.S. Cl. ................. 378/196; 378/195; 378/197; 378/38; 378/39; 378/206; 378/208
(58) Field of Search ................... 378/195, 196, 378/197, 206, 208, 38, 39

(56) References Cited

U.S. PATENT DOCUMENTS 5,123,056 A * 6/1992 Wilson ..................... 382/132
5,692,027 A * 11/1997 Yoshimura et al. .......... 378/38
6,459,760 B1 * 10/2002 D'Ambrosio ................ 378/43
6,463,121 B1 * 10/2002 Milnes ....................... 378/62
6,493,415 B1 * 12/2002 Arai et al. ................... 378/4
6,496,558 B2 * 12/2002 Graumann .................. 378/39
6,510,196 B2 * 1/2003 Lanér ........................ 378/39

* cited by examiner

Primary Examiner—Drew A. Dunn
Assistant Examiner—Allen C. Ho
(74) Attorney, Agent, or Firm—Koda & Androlia

(57) ABSTRACT

An X-ray object positioning apparatus for use in X-ray imaging apparatus which irradiates X-rays an object to be examined to produce an X-ray absorption coefficient of a desired region of the object by means of X-rays transmitted through the object. The X-ray object positioning apparatus comprises a chair for fixing and holding the object; an imaging position moving apparatus for relatively moving an X-ray imaging target area relative to the fixed object chair; and display for variably showing the relative positional relation between an object model corresponding to the object and an imaging target area index corresponding to the X-ray imaging target area. The position between the object and the imaging target area is set by the moving operation for the position between the object model and the imaging target area index on the display, in a manner that the relative positional relation between the object model and the X-ray imaging target area index, both displayed on the display, conforms with the relative positional relation between the object and the X-ray imaging target area, moved by the imaging position moving apparatus.

15 Claims, 17 Drawing Sheets

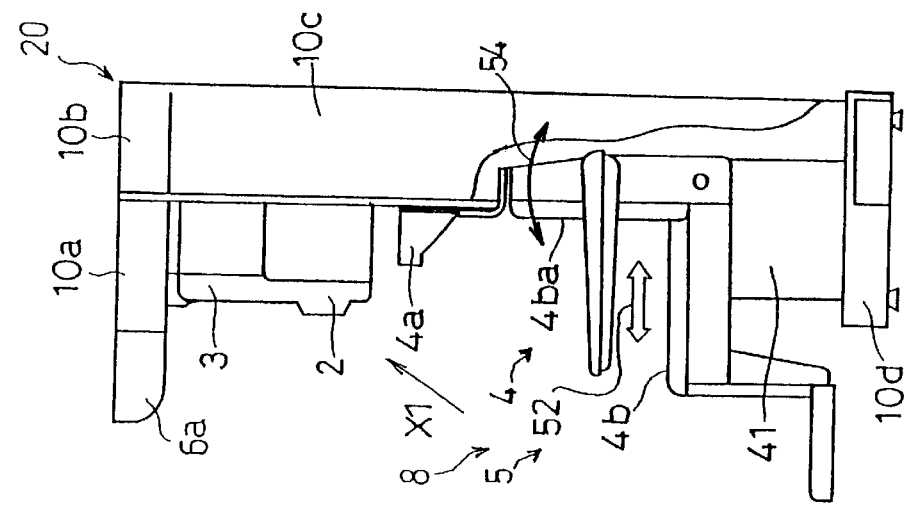
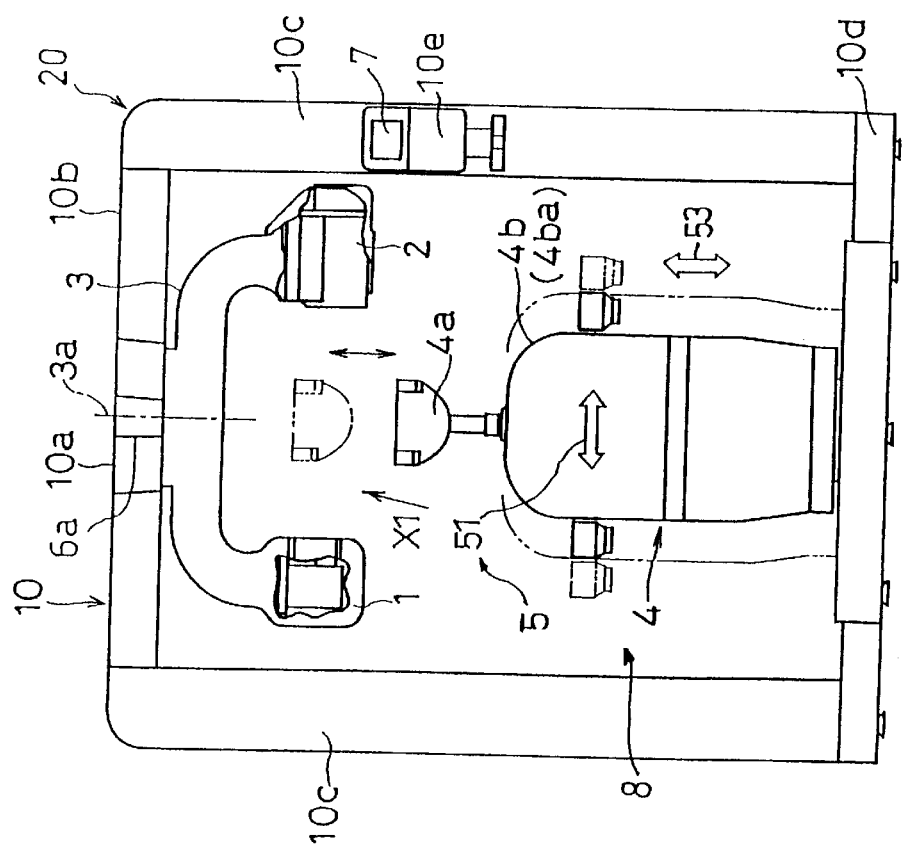
Fig.13a
Fig.13b

X-RAY OBJECT POSITIONING APPARATUS FOR USE IN X-RAY IMAGING APPARATUS AND X-RAY IMAGING APPARATUS PROVIDED WITH THE SAME

BACKGROUND OF THE INVENTION

1. Field of the Invention

The present invention relates to an X-ray object positioning apparatus for use in an X-ray imaging apparatus which radiates X-rays on an object and produces an image of an X-ray absorption coefficient of a desired region of the object by X-rays transmitted through the object and an X-ray imaging apparatus provided with the same.

2. Prior Art

Some X-ray imaging apparatus for executing panoramic radiography of a dental jaw bone in dental field need accurate radiation of X-rays on a desired region of an object. For this purpose, X-ray positioning means for use in an X-ray imaging apparatus for positioning the object at a desired imaging position is used.

One example is an X-ray object positioning means for use in an X-ray imaging apparatus which uses guide beams in X, Y, and Z directions showing X-ray imaging position and sets relative positional relation between the object and an X-ray generator in such a manner that these guide beams are radiated at desired positions of the object.

However, in such a method, it has been advantageous to rough positioning of the whole object or its parts. If X-rays are radiated only on a local region in the object and an X-ray image of that region is required, for example, an image of a few teeth around a carious tooth is required, positioning should be executed depending on guide beams radiated on the outside of the object, which is a human head, and assuming the radiated region inside thereof, thereby enabling accurate positioning.

Furthermore, anatomical knowledge on the radiated region of the object is required for accurate positioning. There has been a problem that only a skilled operator can execute radiography and there has been a high possibility of mistakes.

SUMMARY OF THE INVENTION

The present invention has been proposed in view of the above-mentioned problems. It is an object of the present invention to provide an X-ray object positioning apparatus for use in an X-ray imaging apparatus which can execute positioning accurately without depending on experience and hunch when the radiation region of X-rays, namely an X-ray imaging target area, is in the object body, and to provide an X-ray imaging apparatus provided with this means.

According to the X-ray object positioning apparatus for use in an X-ray imaging apparatus of the first embodiment of the present invention, when an object model is fixedly held by object fixing means and either one of the object fixing means or an X-ray generator for irradiating X-rays toward an X-ray imaging target area, or both of them are moved by imaging position moving means so as to conform the X-ray imaging target area with a predetermined position of the object, position of an imaging target area index is set on an object model, without irradiating guide beams on the surface of the object like prior arts. Positioning is executed in such a manner that a model imaging reference point of the object model and an actual imaging reference point of the object are conformed, then the object model and the imaging target area index are displayed on display means, and position of the imaging target area index is set on the object model while watching that the relative movement of the object is shown as the movement of the imaging target area index against the object model.

Here, the X-ray imaging target area means a target area of X-radiation and has different meanings depending on X-ray imaging methods. It is for example a part of the object on which X-ray radiation beams pass through in case of one-shot imaging. It is a part of the object on which X-ray radiation beams pass through from start to end of scanning in case of scan radiography. Further, in case of panoramic radiography, it is a predetermined area around the movement trace of the rotation center of the rotary arm. As for an ortho X-ray CT radiography, it will be described later. The imaging target area index is the one shown on the display means by employing the X-ray imaging target area as a model.

The object model is that the object using as a model is diagrammatically represented on a plane view and, for example, includes a view wherein the object is comprehended on an one-dimensional coordinate of only a Z-axis, not only the view wherein the object is comprehended on a two-dimensional coordinate of an X-axis and a Y-axis.

Accordingly, comparing with presuming from outside, the position of the X-ray imaging target area in the object can be clearly understood and can be set on an objected local region easily and no mistake without requiring anatomical knowledge and experience on the object.

According to an X-ray object positioning apparatus for use in an X-ray imaging apparatus of the second embodiment of the present invention, in case that an object and an X-ray imaging target area are relatively moved, an object model is moved while an imaging target area index is fixed on the display. Therefore, the movement of the object against the fixed X-ray imaging target area can be comprehended by intuition so that positioning of the object can be easily done with no mistake.

Further according to an X-ray object positioning apparatus for use in an X-ray imaging apparatus of the third embodiment of the present invention, in case that an object and an X-ray imaging target area are relatively moved, an imaging target area index is moved while an object model is fixed on the display. Therefore, when the X-ray imaging target area is smaller than the object, such a display is possible that the imaging target area index is moved within the display area of the object model while the object model is shown on the display, thereby enabling effective usage of the display screen. Moreover, it is easily understood where the imaging target area index is on the object model, namely where it is on the whole object.

In an X-ray object positioning apparatus for use in an X-ray imaging apparatus of the fourth embodiment of the present invention, the relative moving relation between an object model and an imaging target area index on the display is varied in accordance with the relative moving relation between an actual object fixed on an object fixing means and the X-ray imaging target area.

In other words, in case that the object is fixed and the X-ray imaging target area is moved, the object model is fixed and the imaging target area index is moved on the display. On the other hand when the X-ray imaging target area is fixed and the object is moved, the imaging target area index is fixed and the object model is moved also on the display.

Therefore, actual movement of the object conforms to its movement on the display so that movement of the object can be understood by intuition and the object can be easily positioned with no mistake.

In an X-ray object positioning apparatus for use in an X-ray imaging apparatus of the fifth embodiment of the present invention, before positioning an X-ray imaging target area by relatively moving an object and an X-ray imaging target area, an actual imaging standard point of the object and a model imaging standard point of an object model are accorded by means of calibration means. Such defined process is a natural pre-process for accurate positioning and as a result the standard point of the actual object and that of the object model are conformed. Accordingly the movement on the display accords with the actual movement, thereby enabling accurate positioning.

An X-ray object positioning apparatus for use in an X-ray imaging apparatus of the sixth embodiment of the present invention combines guide beams which have been used as positioning means from outside of the object in prior arts. Such guide beams are used as calibration means for according a model imaging standard point of an object model and an actual imaging standard point of the object.

That is, a standard point is selected at a position which is relatively near the object surface, at a root apex of front teeth in case of a dental jaw. Because the rood apex of front teeth corresponds to a side part of front lips seen from outside of the object which is a human head, both standards are considered to be agreed when guide beams conform to the side part of front lips of the object.

In such a manner, calibration can be executed without touching the object and further guide beams can be a rough standard representing the X-ray imaging target area on the object surface, thereby achieving easy comprehension of the target area.

Calibration means isn't limited to such guide beams. A method using a terminal which touches a standard point of front teeth may be employed or a method using a dental articulation model of the object may be executed for purposes of accuracy in dentistry.

An X-ray object positioning apparatus for use in an X-ray imaging apparatus of the seventh embodiment of the present invention is characterized of a relative display way of an object model and an imaging target area index on display means. If the object size is varied, its object model size isn't changed accordingly, but the size of the imaging target area index is changed without changing the displayed size of the object model. Therefore, the image of the area size covered by an X-ray imaging target area against the object size can be easily comprehended, thereby enabling easy judgment of radiation extent.

The display area of the display means is generally limited. However, in such a case mentioned above, the object model size showing the entire area where the imaging target area index is moved can be constant so that the display area of the display means can be effectively used.

An X-ray object positioning apparatus for use in an X-ray imaging apparatus of the eighth embodiment of the present invention is characterized of a relative display way of an object model and an imaging target area index on display means like the seventh embodiment. In this embodiment, the imaging target area index is constant and the object model size is changed unlike the embodiment 7 wherein the imaging target area index is varied in inverse proportion to the object size. Accordingly, such an embodiment is suitable for an actual imaging and the image of the area size covered by an X-ray imaging target area against the object size can be easily comprehended, thereby enabling easy judgment of the extent of radiation. Moreover, the size relation between the object and the object model can be sensuously understood.

According to an X-ray object positioning apparatus for use in an X-ray imaging apparatus of the ninth embodiment of the present invention, a coordinate axis index which defines a central position of an imaging target area index is shown on display means. The central position, the rotation center of a rotary arm for X-ray radiation in case of a panoramic radiography, can be comprehended at ease, thereby achieving usability.

An X-ray object positioning apparatus for use in an X-ray imaging apparatus of the tenth embodiment of the present invention comprises coordinate axis rotation means for rotating a coordinate axis for X-ray object positioning against an imaging standard coordinate system. The coordinate axis after rotation can be a slice standard axis for hewing out sliced sectional images of the obtained three-dimensional X-ray image. In this case because an object model is shown on display means in such a shape along the imaging standard coordinate system, the slice standard axis angle at an imaging position, namely a slice angle, can be set so as to along with the teeth arrangement of a dental arch if the object is a dental arch. Therefore, slice angle setting isn't required to be done again in case of hewn-out display.

Here, the imaging standard coordinate system indicates a coordinate system which becomes an imaging standard of the X-ray imaging apparatus adapted with the X-ray object positioning apparatus. If the object is a human head for example, a median line of the human body becomes a standard, its vertical direction is a Z-axis, its lateral direction for the object is an X-axis, and its back and forth direction for the object is a Y-axis. Its original point can be an occlusal surface of the dental arch of the objects head on the median line.

According to an X-ray object positioning apparatus for use in an X-ray imaging apparatus of the eleventh embodiment of the present invention, in case that an object to be radiated is a dental jaw bone as one of special examples, its vertical positional arrangement is possible up to a maxillary antrum. Such an apparatus meets the requirements of actual diagnosis.

In an X-ray object positioning apparatus for use in an X-ray imaging apparatus of the twelfth embodiment of the present invention, the X-ray imaging apparatus provided with the X-ray object positioning apparatus is limited to an ortho X-ray computed tomography apparatus.

The ortho X-ray CT apparatus has been proposed by the applicant of the present invention and its details are described in JP-A-2000-139902. According to the apparatus, conical X-ray beams are locally radiated only on a local region of an object while rotating a rotary arm suspending an X-ray generator and a two-dimensional image sensor opposed each other. Its imaging condition is such that conical X-ray beams covering only the local region to be pictured are radiated from the X-ray generator and the rotary arm is driven to be rotated while fixing a rotation center on the center of the local region to be pictured.

The electrical signals on the two-dimensional X-ray imaging sensor obtained by thus radiating are digitalized and backprojected so as to obtain a three-dimensional X-ray absorption coefficient of the irradiated local region, thereby obtaining optional sectional images of the local region. Further according to this, the exposed dose of X-rays can be reduced to a few tenths or a few hundredths compared to the prior art which radiates X-rays on the entire object.

This imaging method is based on an idea that the projection data of the local region on which conical X-ray beams are locally radiated is always obtained, but the conical X-ray beams temporally transmit the other area surrounding the local region according to rotation compared to the local region and there is only a minute affection on the projected data, so that the affection on the projection data other than the local region can be almost ignored in case of backprojection.

The X-ray object positioning apparatus of the present invention is suitable for positioning in case of local radiation which is considered to be most important for such an ortho X-ray CT apparatus.

Further according to the X-ray object positioning apparatus of the present invention, the object is limited to a dental jaw bone and the X-ray imaging target area is limited to the area which is always locally radiated. In such a case requirements for X-ray imaging target area positioning is largest and the effects of the present invention can be highly brought out.

An X-ray object positioning apparatus for use in an X-ray imaging apparatus of the thirteenth embodiment of the present invention is the twelfth embodiment having the characteristics of the eleventh embodiment so that both effects of the embodiments can be multiply achieved.

An X-ray imaging apparatus of the fourteenth embodiment of the present invention is provided with an X-ray object positioning apparatus having the characteristics of the first to the thirteenth embodiments so that each effect of the positioning apparatuses can be exerted as an imaging apparatus.

An X-ray imaging apparatus of the fifteenth embodiment corresponds to the X-ray imaging apparatus providing the X-ray object positioning apparatus having the characteristics of the fourteenth embodiment, namely the X-ray object positioning apparatus of the twelfth and the thirteenth embodiments. The X-ray imaging apparatus has the characteristics of these embodiments as an imaging apparatus.

BRIEF DESCRIPTION OF THE DRAWINGS

FIG. 13a is a front view of an X-ray imaging apparatus provided with the X-ray object positioning apparatus for use in an X-ray imaging apparatus of the present invention and FIG. 13b is its side view, a part of which is broken.

DETAILED DESCRIPTION OF THE INVENTION

Embodiments of the present invention will be explained referring to the attached drawings.

FIG. 1 is a conceptual diagram of one embodiment of an object positioning method according to the X-ray imaging apparatus of the present invention. Hereafter, a case wherein an X-ray object positioning apparatus for use in an X-ray imaging apparatus is provided for an X-ray computed tomography (CT) apparatus for X-ray imaging a head of a human body is explained.

Figure 1A:
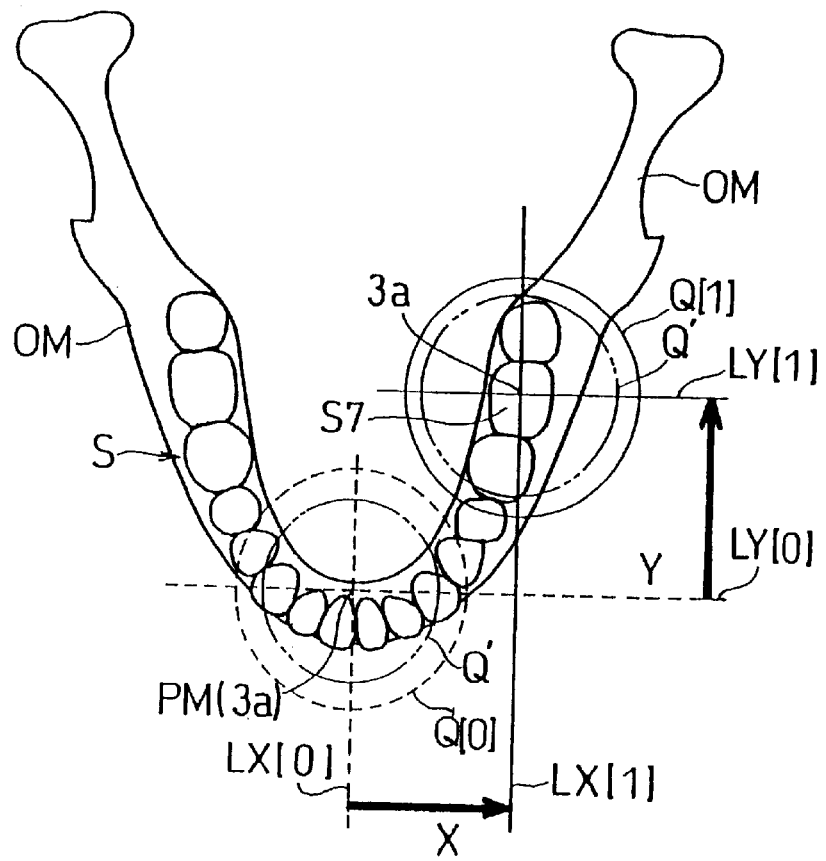
FIG. 1 is a conceptual diagram of one embodiment of an object positioning method according to the X-ray imaging apparatus of the present invention.
Figure 1B:
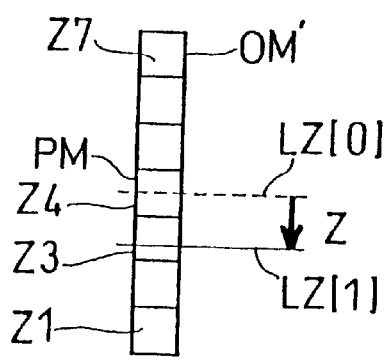

FIG. 1a and FIG. 1b show object's models OM, OM$^1$ shown on the display of the X-ray object positioning apparatus for use in an X-ray imaging apparatus (see display 7 in FIG. 13). In the figures an example wherein an object is a dental jaw bone of a human head is used and its diagram illustrating a dental arch of the dental jaw bone is shown as the object model.

In FIG. 1a the object model OM has an object model projection point PM, which is a root apex of front teeth in the figure.

The reference numbers LX, LY are a crosswise guide beam and a lengthwise guide beam respectively. LX is a guide beam showing an X-ray imaging position in X direction, namely in crosswise direction against the object. LY is a guide beam showing an X-ray imaging position in Y direction, namely in lengthwise direction against the object. The figure shows where these guide beams are positioned on the object model OM shown on the display.

The reference mark S is a dental arch and a tooth S7 is an imaging target of the dental arch S, namely a target tooth of dental care. The mark Q is a target area of X-ray imaging, in this case, when the above-mentioned ortho X-ray CT (local X-ray radiation CT) is executed as an X-ray imaging method. The mark Q is an area where X-rays are always locally radiated during CT imaging and its center is a rotation center 3a of a rotary arm which is rotated with an X-ray generator and a two-dimensional image sensor facing each other.

In case of this ortho X-ray CT, an actual size of the imaging target area index Q is fixed, for example its diameter is 40 mm and its height is 30 mm, which is a suitable size for obtaining a partial X-ray image of a dental jaw bone. However, the size is appropriately selected.

If specifically required to be distinguished, when the crosswise guide beam LX, the lengthwise guide beam LY and the imaging target area index Q are model imaging reference points, they are shown as the crosswise guide beam LX[0], the lengthwise guide beam LY[0] and the imaging target area index Q[0] respectively. When they are at an imaging target point, they are shown as the crosswise guide beam LX[1], the lengthwise guide beam LY[1] and the imaging target area index Q[1].

In this method, before displaying by the displaying means, calibration is executed such that an actual imaging reference point (root apex of front teeth in this case) of the object (dental jaw bone of a human body in this case) is agreed with the model imaging reference point of the object model.

Specifically, the object is fixed with an object fixing means (see reference number 4 in FIGS. 13a and 13b) and a relative position of the guide beam and the object is moved in such a manner that the position of the root apex of the object's front teeth is radiated by the guide beam while the object is thus fixed. Hereby the rotation center 3a of the rotary arm agrees with the actual imaging reference point.

When such a calibration is executed in advance, the reference points of the actual object and the displayed object model are agreed and the movement on the display accords with the actual movement, thereby achieving an accurate positioning.

Upon finishing the calibration, a display is shown such that the model imaging reference point PM of the object model OM and the rotation center 3a of the rotary arm are agreed as shown in dotted lines in the figure.

When the object is moved in crosswise (X direction in the figure) and in lengthwise (Y direction in the figure) in this embodiment, its moving conditions are reflected on the display as positional changes of the imaging target area index Q and the guide beams LX, LY. Therefore, positioning of the imaging target area index Q can be executed only by preferably covering the target tooth S7 by the target index Q on the display, namely by moving the intersection point of the guide beams Lx, LY (rotation center 3a of the rotary arm) on the tooth S7.

Thus set imaging target area index Q[1] can get a desired tooth accurately. X-ray images substantially corresponding to medical objects and preferably showing medical target areas can be obtained by executing X-ray imaging under such a condition.

Accordingly, comparing with an external presuming, anatomical data are shown by an object model so that a position of the X-ray imaging target area in the object can be clearly be recognized and anatomical knowledge and experience about the inside of the object aren't required. Therefore, the X-ray imaging target area can be positioned at a target local area.

In the above-mentioned embodiment, it is explained that the display follows the movement of the object. Contrary the movement of the object may follow the movement on the display of the imaging target area index Q shown on the display. Otherwise, the object may be moved by giving a movement command after finally positioning the imaging target area index Q[1] on the display.

The actual size of the object in this figure, that is the size of the dental arch, is varied depending on the object, namely an adult or a child. The size on the display against the object model OM is determined so as to keep the ratio of the actual size of the imaging target area index Q for the size of the dental arch. Therefore, when the object is larger, the display means shows an imaging target area index $Q^1$ (shown with a chain double-dashed line) smaller than the imaging target area index Q shown with a dotted line or a solid line.

Accordingly, a relative size relation between the actual object and the imaging target area index Q with a fixed size can be clearly seen without changing the display size of the object model OM. Therefore, a size image of the area covering the X-ray imaging target area against the object's size can be easily understood and an operator can judge with ease that X-rays are radiated to which area.

Furthermore, although the display area of the display means is generally limited, if a display is shown while the size and position of the object model are fixed on the display and the imaging target area index is moved thereon, the display area can be effectively used.

The object model $OM^1$ shown in FIG. 1b is a simple type used for moving the imaging target area index vertically against the object and its vertical positions to be determined are shown in seven stages from Z1 to Z7.

After such a calibration, it is shown that a vertical guide beams LZ[0] corresponds to the vertical position Z4 which is the object model projection point PM in vertical direction (Z direction in the figure) as shown with dotted lines in the figure.

When the object is moved as mentioned above, the condition is shown by the minute as positional change of the vertical guide beam LZ. Watching the condition, the object is stopped moving when the guide beam LZ[1] reaches the vertical point L3 which is a target of the vertical guide beam LZ[1]. Hereby the vertical positioning of the X-ray imaging target area is completed.

If the object is a dental jaw bone of a human body which is used in this embodiment, such vertical positioning may be executed roughly and positioning of the X-ray imaging target area can be executed more easily by means of such an object model.

Figure 2:
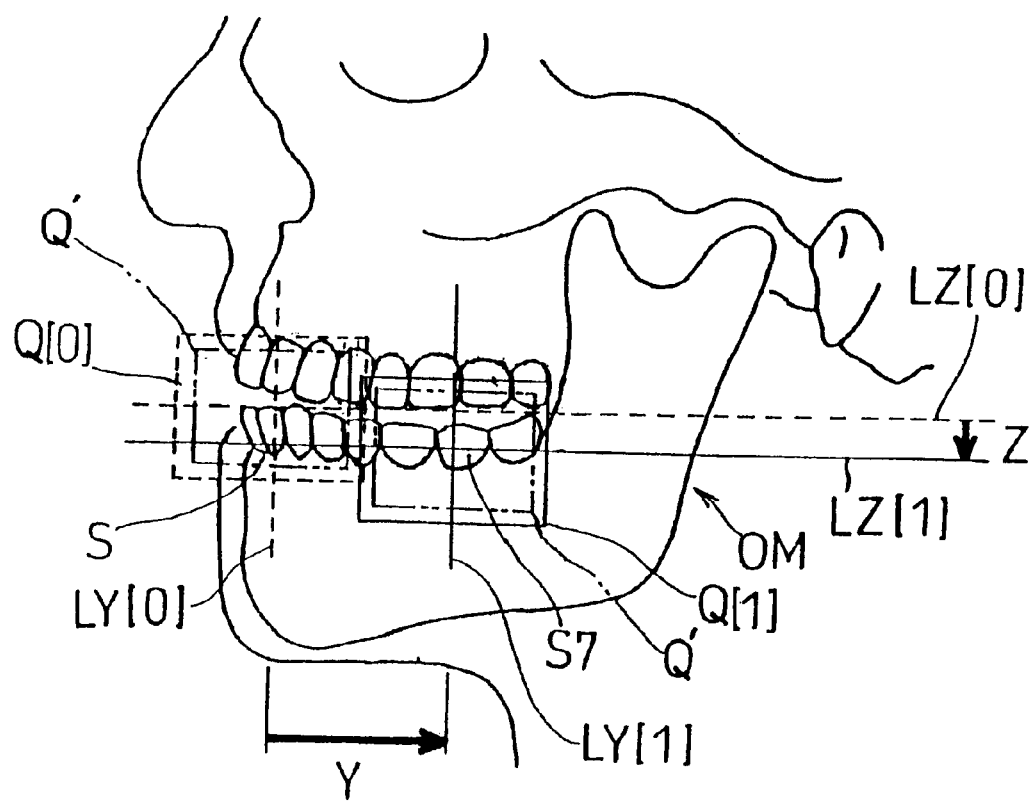
FIG. 2 is a conceptual diagram of other embodiment of an object positioning method according to the X-ray imaging apparatus of the present invention.

FIG. 2 is a conceptual diagram of other embodiment of an object positioning method according to the X-ray imaging apparatus of the present invention.

This embodiment uses a dental jaw bone of a human body as an object and the object model OM is more truly illustrated.

When such a object model OM is used, a lengthwise image can be displayed as shown in the figure so that the radiating region of the imaging target area index Q can be more clearly recognized from an anatomical point of view.

In this case the soft tissue of skin is also shown as an object model other than the hard tissue such as a dental jaw bone, thereby enabling more practical recognition. Such an object model with the soft tissue can be applied to FIG. 1a and the same effect can be achieved.

In FIG. 1 the dental arch is illustrated two dimensionally and the imaging target area index Q is shown as a circle.

However, it may be shown three dimensionally as a perspective view and the index Q may be shown as a perspective view of a column. Furthermore, the shape showing the imaging target area index may be the actual shape used for ortho X-ray CT.

Figure 3:
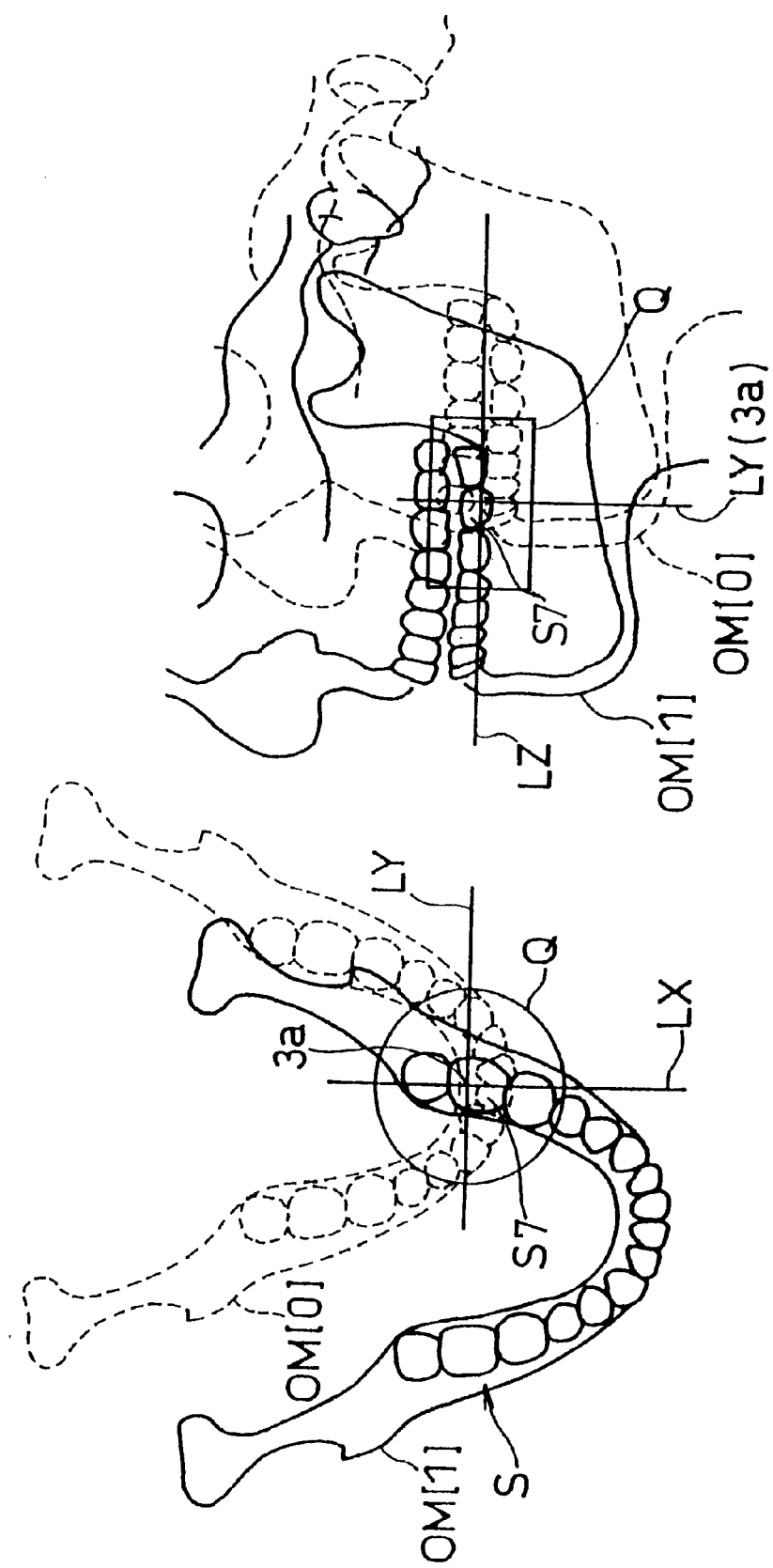
FIG. 3 is a conceptual diagram of still other embodiment of an object positioning method according to the X-ray imaging apparatus of the present invention.

FIG. 3 is a conceptual diagram of still other embodiment of an object positioning method according to the X-ray imaging apparatus of the present invention. The same reference numerals are allotted to the members which have been already explained and there explanations are omitted hereinafter.

FIG. 3 diagrammatically shows an image shown on the display 7 like FIG. 1 and FIG. 2. In this figure, the imaging target area index Q is fixed, not moved, for positioning the index Q against the object model OM unlike FIG. 1 and FIG. 2. The object model OM is designed to be moved from a position OM[0] where the index Q corresponds to an object model imaging reference point (shown with dotted line) to a position OM[1] where the index Q corresponds to the imaging target point (shown with solid lines).

In this way the movement of the object for the fixed imaging target area index Q can be understood by intuition so that positioning of the object can be done easily and without mistake.

When the relative moving relation of the object model OM and the imaging target area index Q is to be corresponded with the relation of the actual object and the imaging target area index on the display means 7, namely the object is fixed and the imaging target area index is moved, the object model view is fixed and the imaging target area index is moved also on the display. On the other hand, when the imaging target area index is fixed and the object is moved, the target area index is fixed and the object model view is moved also on the object. Accordingly the actual movement of the object and its movement on the display become the same so that positioning of the object can be done easily and without mistake.

Also in this figure, the top view of the object and its side view are shown together. As the result, a three-dimensional movement setting can be easily understood. However, they may be shown separately like FIG. 1a and FIG. 2. Otherwise FIG. 1a and FIG. 1b may be combined and displayed as shown in FIG. 4–FIG. 10.

Figure 4A:
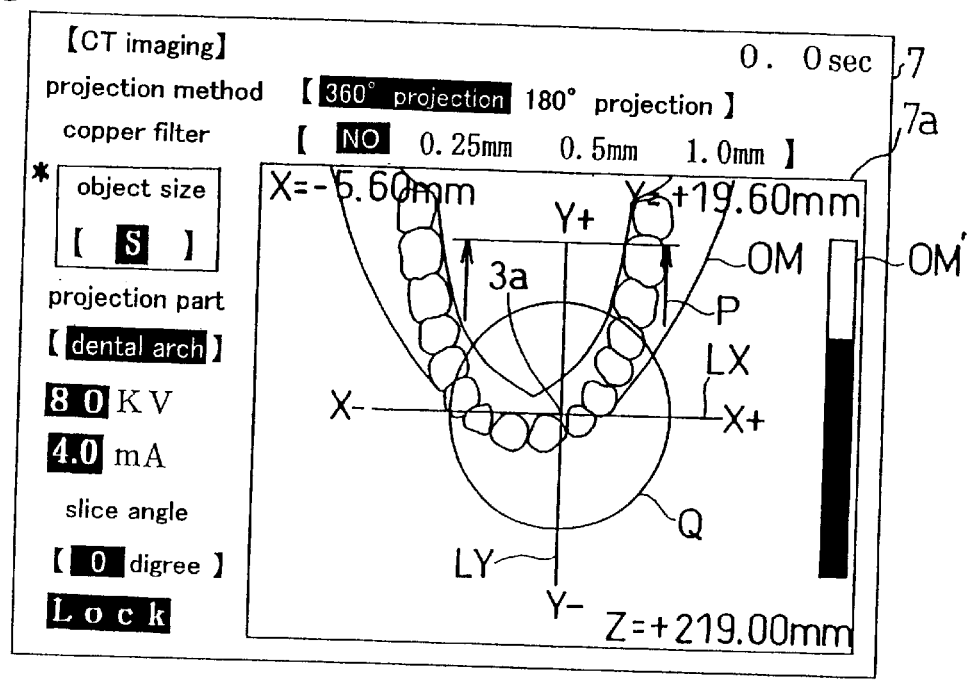
FIG. 4a and FIG. 4b are conceptual diagrams showing a display example of other embodiment of an object positioning method according to the X-ray imaging apparatus of the present invention.
Figure 4B:
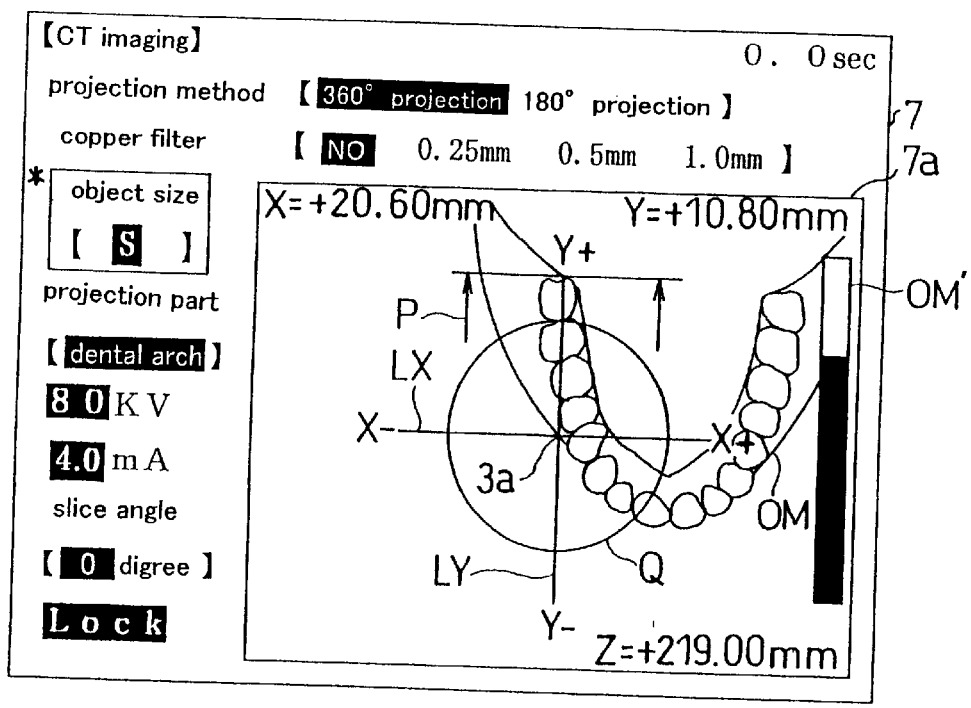

FIG. 4a and FIG. 4b are conceptual diagrams showing a display example of other embodiment of an object positioning method according to the X-ray imaging apparatus of the present invention.

These figures are examples of a display shown on the actual display 7 showing several types of guide massage required for X-ray imaging. Here only the part directly relating to the present invention is explained hereinafter.

The display is a liquid crystal in this embodiment, and its one part is an image display 7a for positioning and guide messages are shown around the display 7a. For those messages required values or data are inputted properly and selection instructions are given by operation means, not shown.

The object models OM, OM$^{1,}$ the imaging target area index Q, and the guide beams LX, LY are shown on the image display 7a. The guide beams LX, LY are called as an coordinate axis index LX, LY respectively which are understood as a coordinate axis index defining the center 3a of the imaging target area index Q hereinafter through FIG. 10.

"X=−5.60 mm", "Y=+19.60", at the right and the left of the upper part on the display 7a and "Z=+219.00 mm" at the lower right on the display 7a show a position of the center 3a of the imaging target area index Q by the distance from the origin on the imaging standard coordinate system. The reference number P shows an X-ray emitting direction.

"S" is shown as a patient size in FIG. 4a and FIG. 4b. The position of the imaging target area index Q isn't changed in FIG. 4b referring to FIG. 4a so that it is understood that the object model OM is moved.

When the object is moved for positioning, the object model OM is also moved on the display. Accordingly the moving direction of the object and that of the object model on the display are corresponded, thereby enabling easy movement setting operation.

The image display 7a shows coordinate axis indexes LX, LY which show the center 3a of the imaging target area index Q. Therefore, the center, which is a rotation center of a rotary arm for emitting X-rays in case of a panoramic radiography, can be easily recognized, thereby achieving good usability.

Figure 5A:
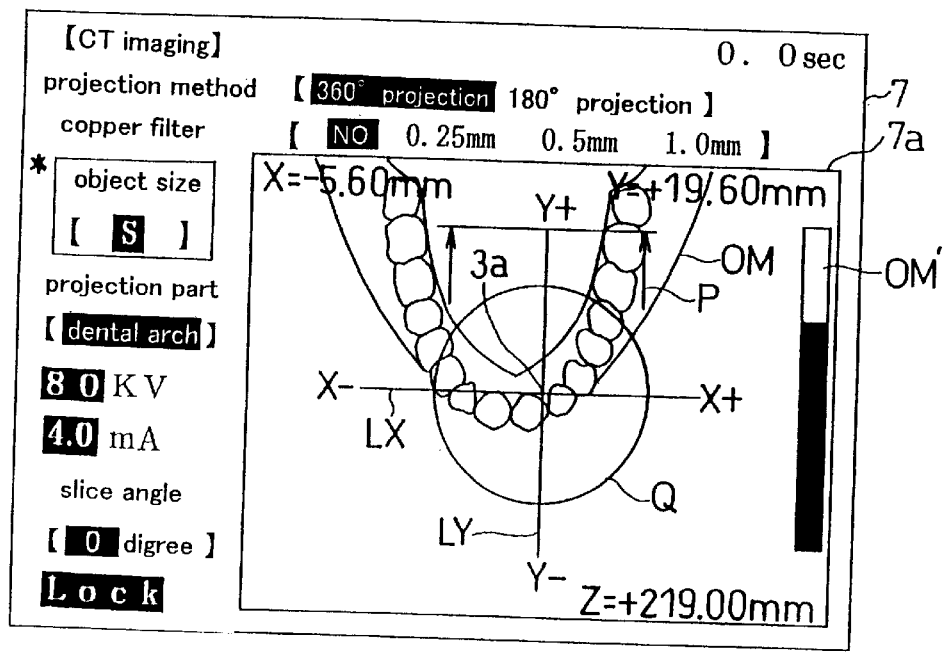
FIG. 5a and FIG. 5b are conceptual diagrams showing a display example of other embodiment of an object positioning method according to the X-ray imaging apparatus of the present invention.
Figure 5B:
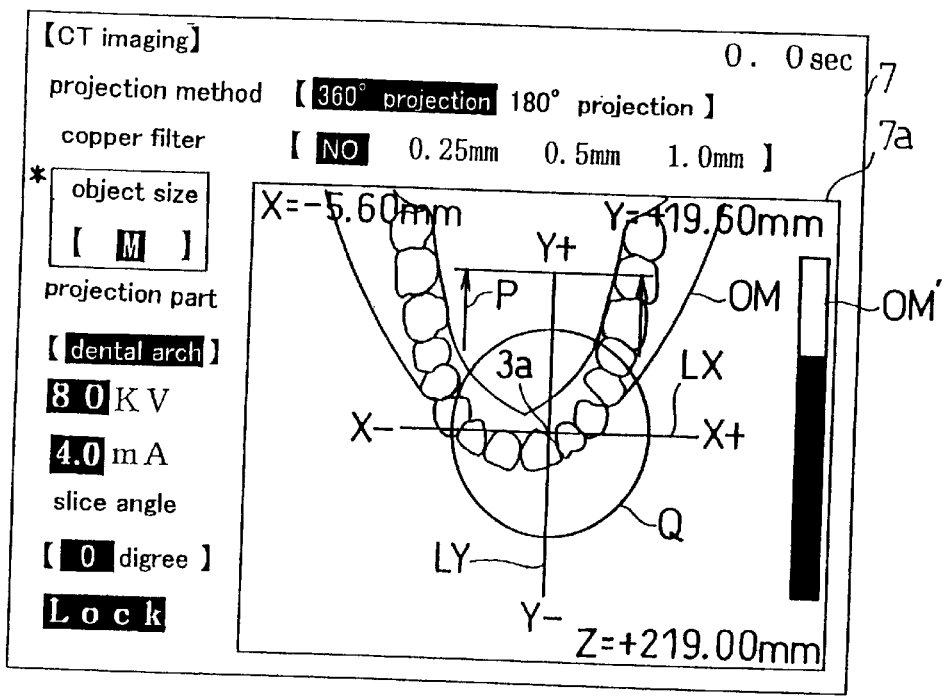
Figure 6A:
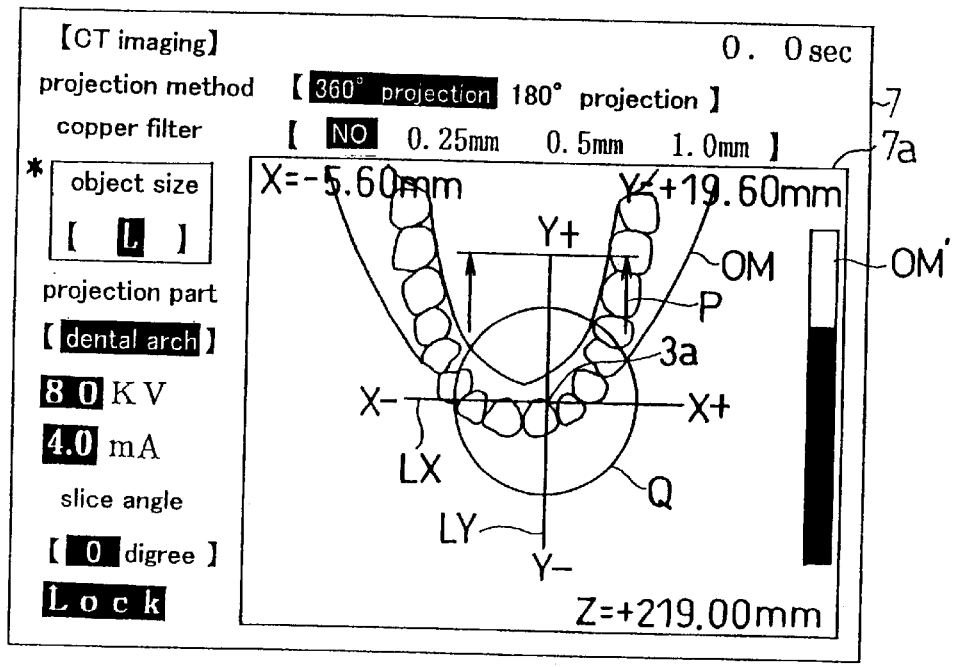
FIG. 6a and FIG. 6b are conceptual diagrams showing a display example of other embodiment of an object positioning method according to the X-ray imaging apparatus of the present invention.
Figure 6B:
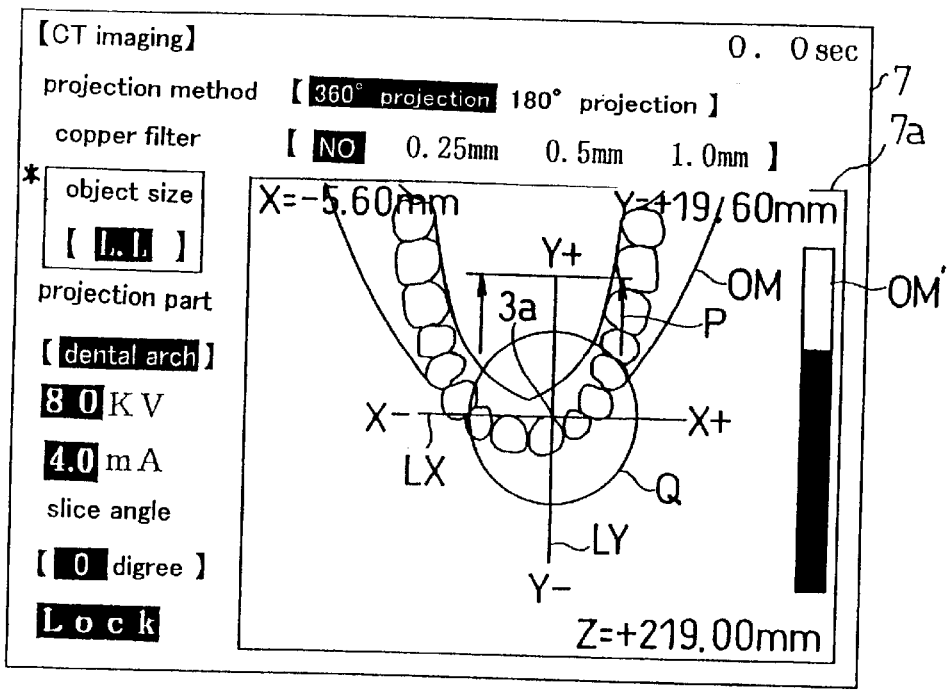

FIG. 5a and FIG. 5b are conceptual diagrams showing a display example of other embodiment of an object positioning method according to the X-ray imaging apparatus of the present invention. FIG. 6a and FIG. 6b are conceptual diagrams showing a display example of other embodiment of an object positioning method according to the X-ray imaging apparatus of the present invention.

Comparing FIG. 5a, FIG. 5b, FIG. 6a and FIG. 6b, only the patient size, which is a setting item, is changed from "S" to "M" to "L" to "LL". Correspondingly, the size of the object model OM isn't changed on the image display 7a and the size of the imaging target area index Q inversely becomes small.

In this way, while the size of the object model OM is set so as to be displayed entirely on the image display 7a of which the size is limited and the size of the imaging target area index Q becomes smaller. Therefore, the size relation of the X-ray imaging target area for the actual object can be clearly comprehended.

Figure 7A:
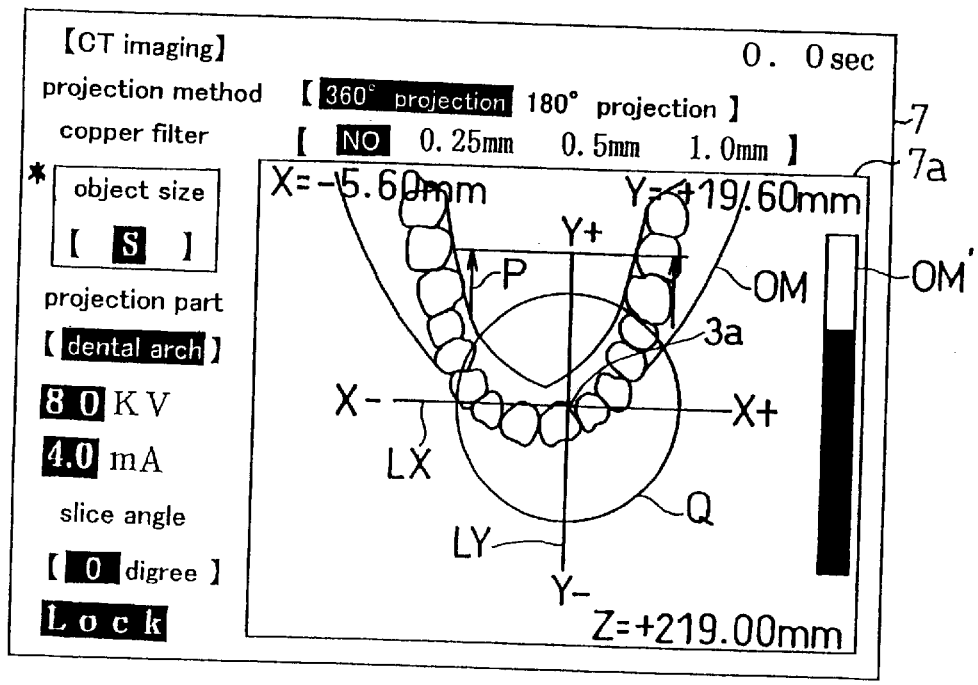
FIG. 7a and FIG. 7b are conceptual diagrams showing a display example of other embodiment of an object positioning method according to the X-ray imaging apparatus of the present invention.
Figure 7B:
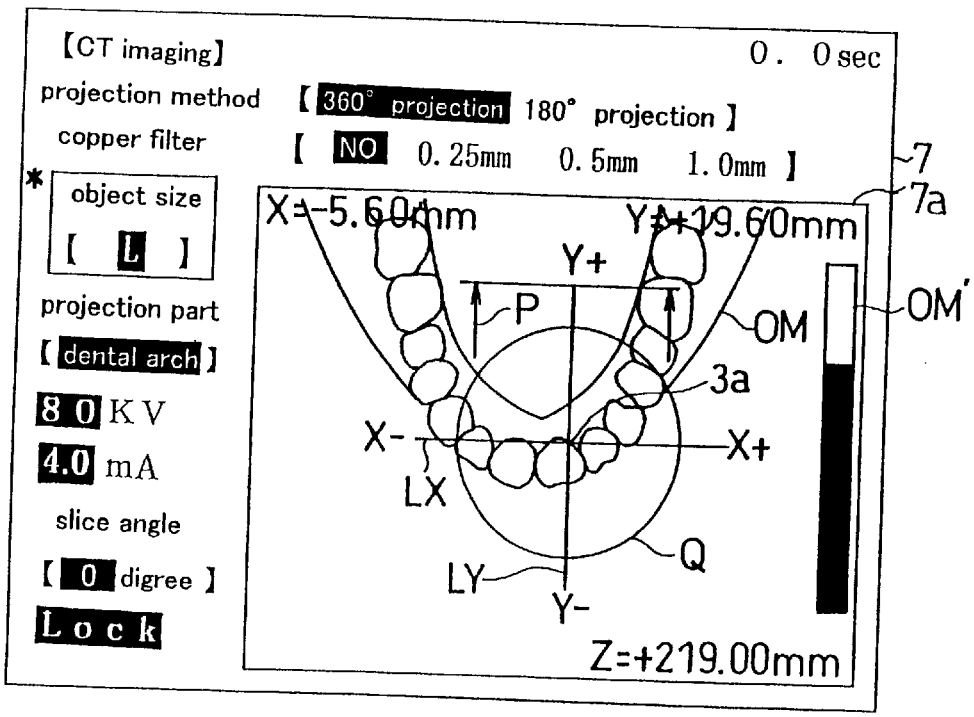

FIG. 7a and FIG. 7b are conceptual diagrams showing a display example of other embodiment of an object positioning method according to the X-ray imaging apparatus of the present invention.

Comparing FIG. 7a with FIG. 7b, only the patient size is changed from "S" to "L", but the size of the imaging target area index Q isn't changed. It can be understood that the size of the object model OM is changed corresponding to the patient size.

Such a manner accords with an actual radiography so that the image of the area size covering the X-ray imaging target area for the object size is recognized and it is easily interpreted to which area X-rays are radiated. Furthermore, the size relation of the object and the object model is sensuously understood.

Figure 8A:
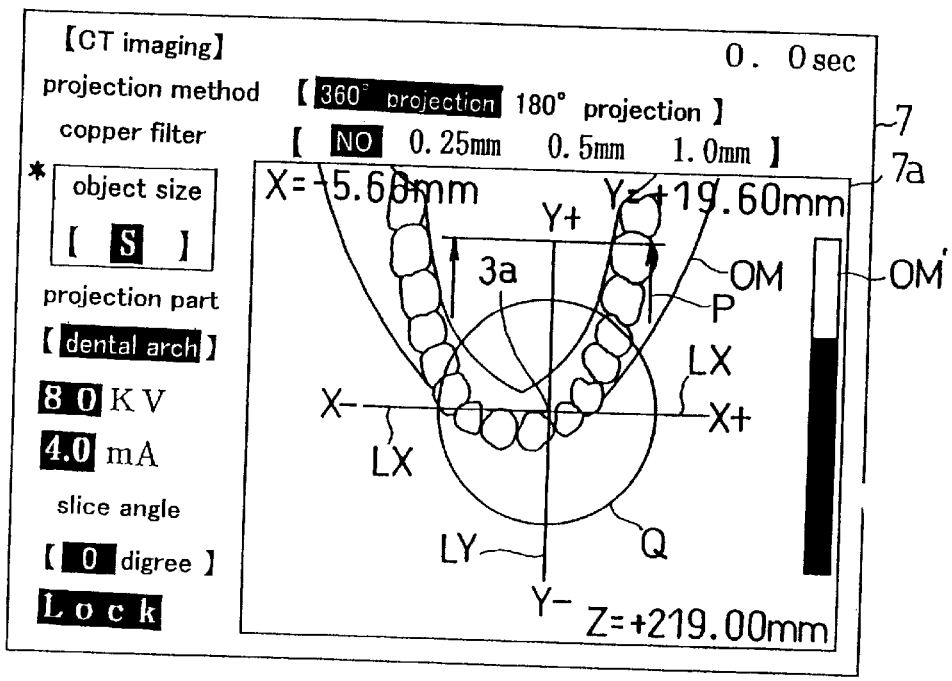
FIG. 8a and FIG. 8b are conceptual diagrams showing a display example of other embodiment of an object positioning method according to the X-ray imaging apparatus of the present invention.
Figure 8B:
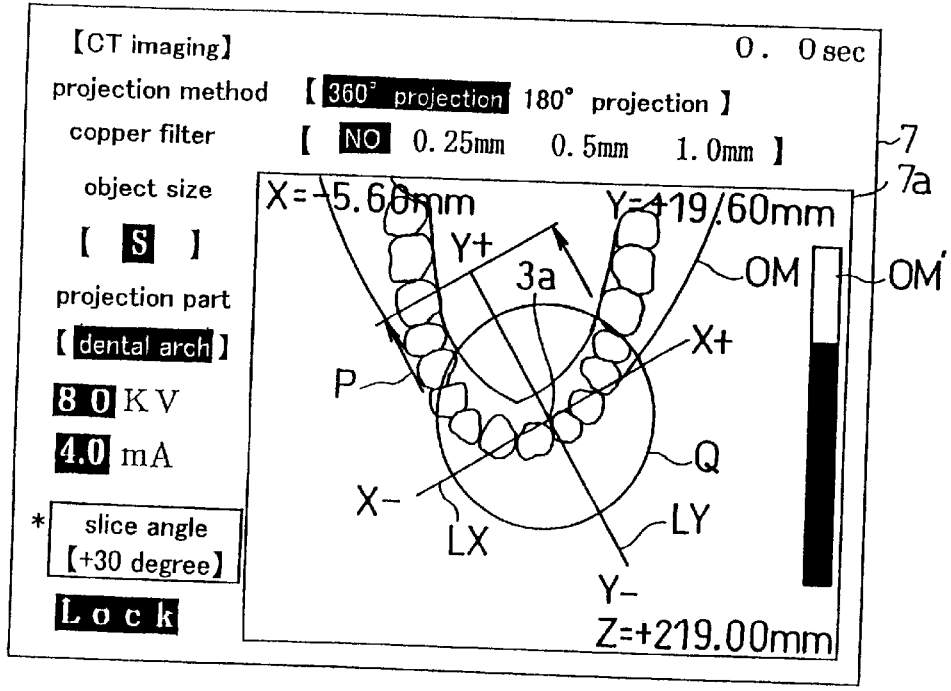

FIG. 8a and FIG. 8b are conceptual diagrams showing a display example of other embodiment of an object positioning method according to the X-ray imaging apparatus of the present invention.

Comparing FIG. 8a with FIG. 8b, a slice angle, which is one of setting items, is changed from "0 degree" to "+30 degree" and it is understood that the coordinate axis indexes LX, LY are correspondingly rotated.

According to the center 3a of the imaging target area index Q in this figure, when the coordinate axis indexes LX, LY are thus rotated, the direction of the coordinate axis index LX agrees with the teeth alignment of the dental arch included in the imaging target area index Q. When a slice image is hewn out from a three-dimensional X-ray image which is obtained after along such coordinate axis indexes LX, LY, such an image becomes suitable for a diagnosis purpose. The slice angle can be set while watching a required image for setting an angle in case of hewing a slice image, thereby accomplishing convenience.

Coordinate axis rotating means is comprised of "slice angle", which is a setting item on the display, and corresponding setting means of the X-ray radiography apparatus.

Figure 9A:
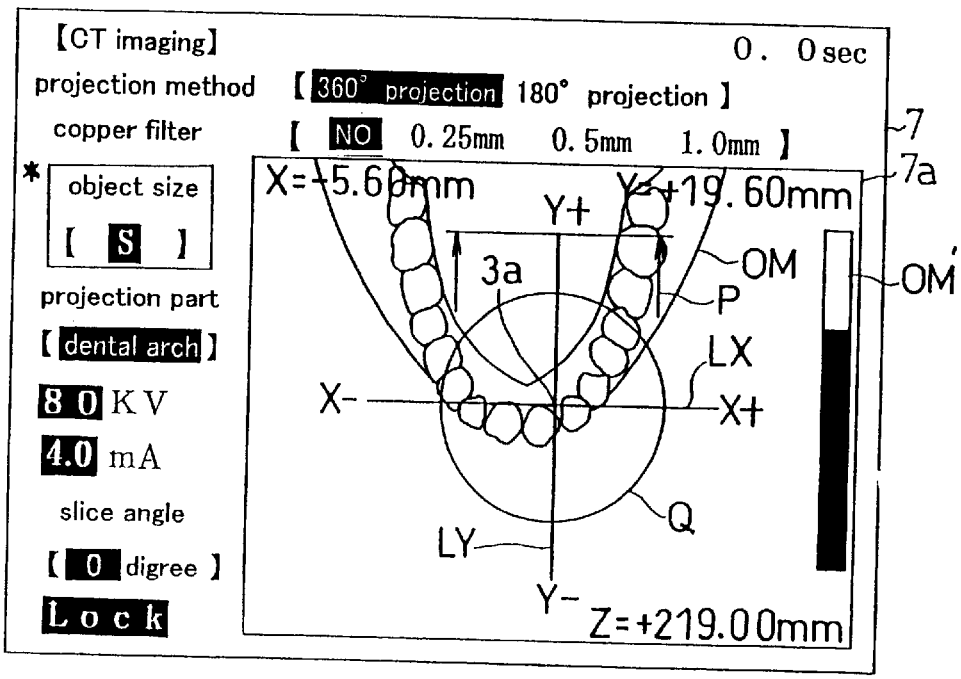
FIG. 9a and FIG. 9b are conceptual diagrams showing a display example of other embodiment of an object positioning method according to the X-ray imaging apparatus of the present invention.
Figure 9B:
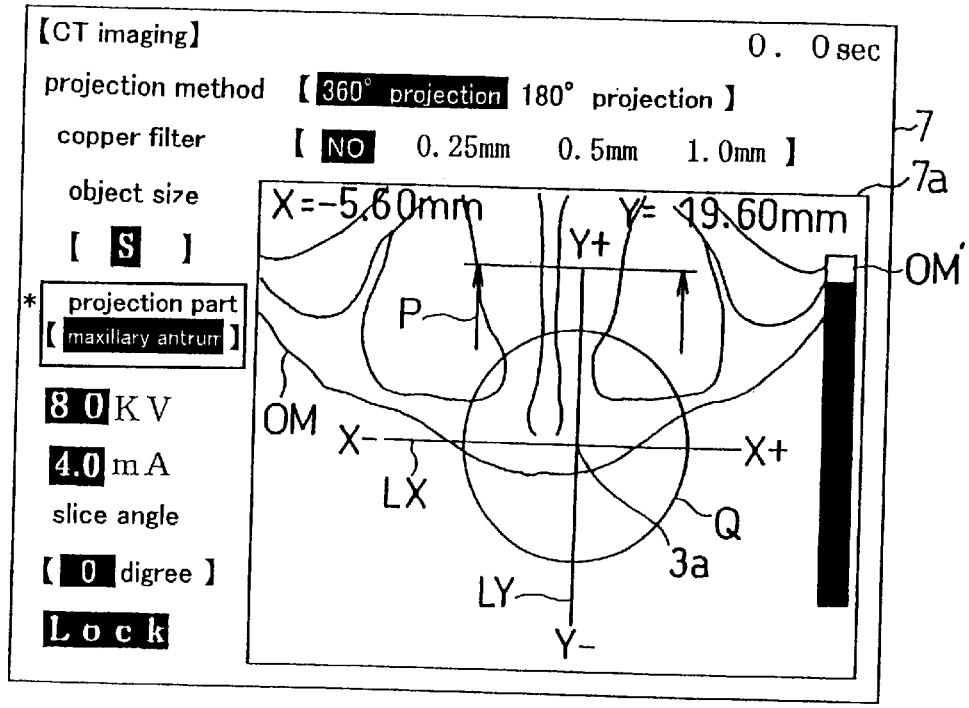

FIG. 9a and FIG. 9b are conceptual diagrams showing a display example of other embodiment of an object positioning method according to the X-ray imaging apparatus of the present invention.

Comparing FIG. 9a with FIG. 9b, only a radiographic area, which is one of setting items, is changed from "tooth row" to "maxillary antrum".

According to this X-ray radiography positioning means, its vertical positioning is possible to the maxillary antrum so that it is suitable for an actual diagnosis.

Figure 10A:
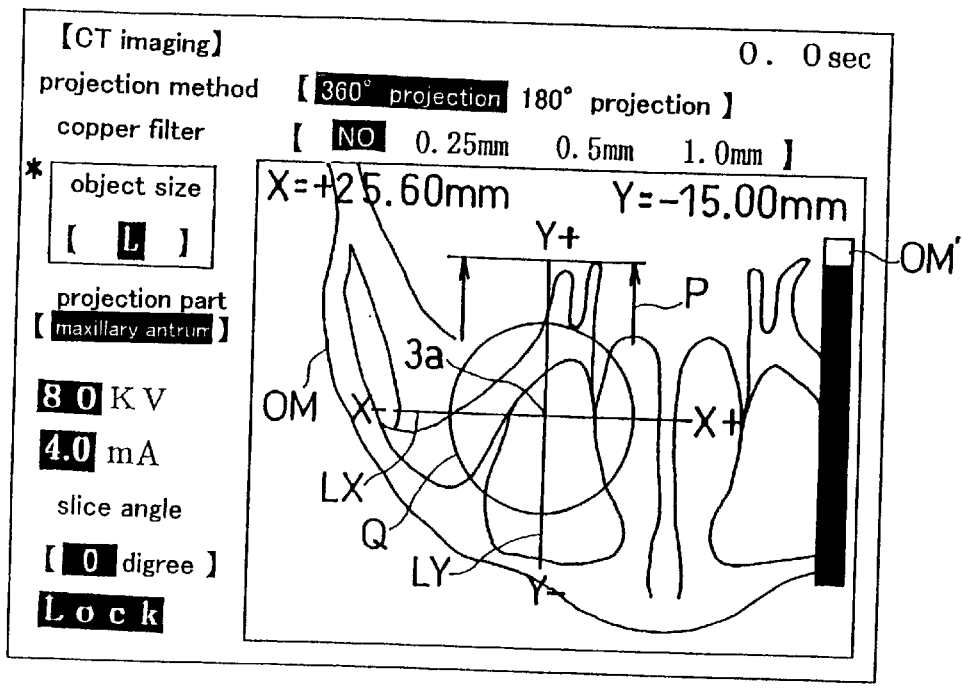
FIG. 10a and FIG. 10b are conceptual diagrams showing a display example of other embodiment of an object positioning method according to the X-ray imaging apparatus of the present invention.
Figure 10B:
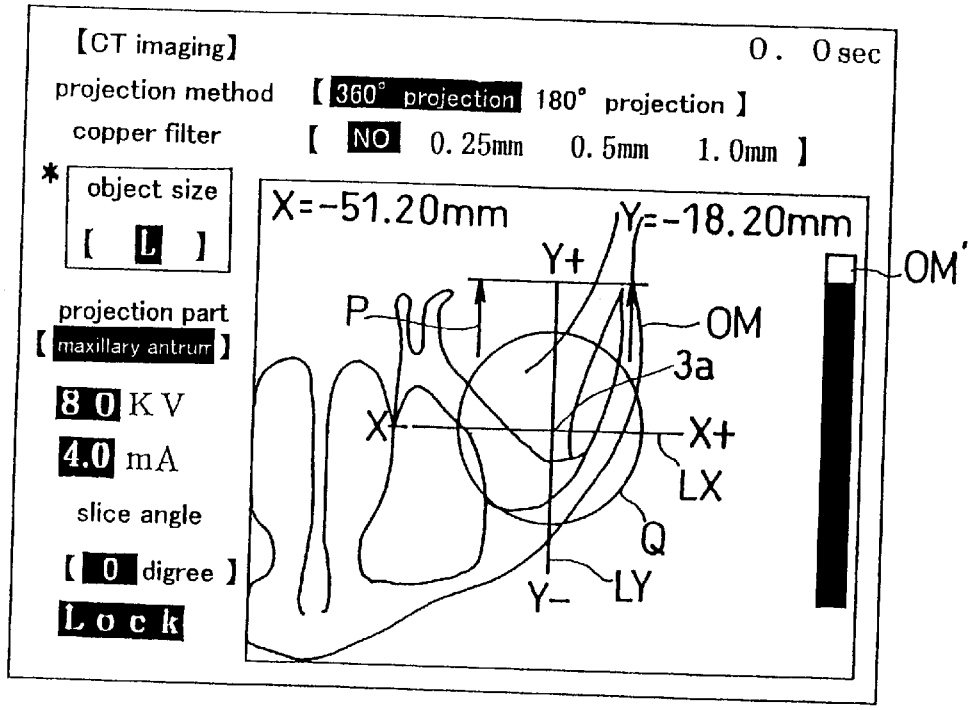

FIG. 10a and FIG. 10b are conceptual diagrams showing a display example of other embodiment of an object positioning method according to the X-ray imaging apparatus of the present invention.

Comparing FIG. 10a with FIG. 10b, the patient size "L" and the radiographic area "maxillary antrum" aren't changed, further the position of the imaging target area index Q isn't changed, so that it is understood that only the object model OM is moved.

Positioning of the maxillary antrum can be done on the image display 7a while moving the object model OM. Of course, positioning of the maxillary antrum can be also done while fixing the object model OM and moving the imaging target area index Q as shown in FIG. 1 and FIG. 2.

Next, structural parts constituting the X-ray object positioning apparatus according to the present invention will be detailed.

Figure 11A:
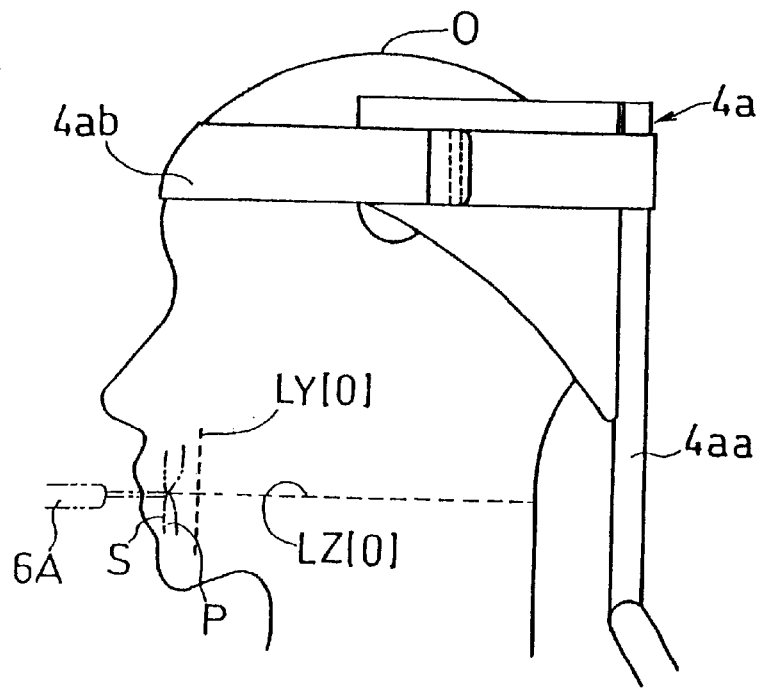
FIG. 11a is a side view showing that an object is fixedly held on an object fixing means according to the X-ray object positioning apparatus for use in X-ray imaging apparatus of the present invention and FIG. 11b is a perspective view showing how calibration means is used.
Figure 11B:
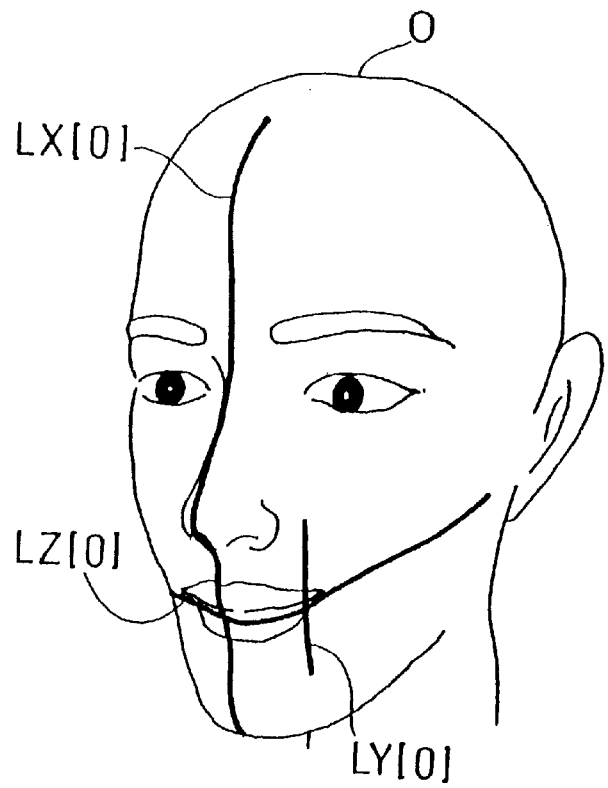

FIG. 11a is a side view showing that an object is fixedly held on an object fixing means according to the X-ray object positioning apparatus for use in an X-ray imaging apparatus of the present invention and FIG. 11b is a perspective view showing how calibration means is used.

The reference numeral 4a in FIG. 11a is head fixing means constructing object fixing means (explained later) and is provided with a support 4aa fixed on the upper part of a main part of the object fixing means and a head fixing band 4ab provided for the support 4aa.

The reference character O is an object and a direct X-ray radiation target is a human head. The characters LY, LZ are a lengthwise guide beam and a vertical guide beam respectively which have been already explained. The crosswise guide beam LX which is seen in FIG. 11b isn't shown in FIG. 11a because it appears on its side view.

In the perspective FIG. 11b, all the guide beams LX, LY and LZ are shown.

The guide beams LX, LY, LZ have been conventionally used for an X-ray imaging apparatus. Positioning of the object and the X-ray imaging target area has been done roughly depending on where the guide beams radiated on the object surface are set.

According to the present invention, it has been already explained in FIG. 1a that the guide beams LX, LY, LZ are used as calibration means for according the imaging reference point P of the object O and the object model imaging reference point PM of the object model OM.

In this embodiment, relative positions between the guide beams are moved by moving the object fixing means with the head fixing means 4a against the guide beams LX, LY, LZ. As for the guide beams LX, Ly or the vertical guide beam LZ, calibration can be done by moving the guide beams LX, LY to the actual imaging reference point P of the object O in case of applying the method of FIG. 1b.

When such guide beams are provided to be used as calibration means, calibration can be executed without touching the object and further the guide beam itself becomes a rough standard showing the X-ray imaging target area on the external surface of the object, thereby enabling easy comprehension of the target area.

Calibration means 6A comprised of a terminal shown in FIG. 11a can be used instead of the guide beams.

Such calibration that the actual imaging reference point P of the object O and the object model imaging reference point PM of the object model OM are agreed can be done by bringing the terminal into contact with the reference point P.

If more accuracy is required, a dental articulation model corresponding to an object may be used for a calibration.

Furthermore, an automatic calibration method can be employed, wherein an actual imaging reference point is detected by a detector and an object or a rotary arm is moved by driving moving means as described as an automatic positioning device of an X-ray panoramic imaging apparatus in JP-A-2-140150 unlike the above-mentioned calibration method wherein the X-ray imaging target area is moved by the moving means referring to the calibration method.

Figure 12A:
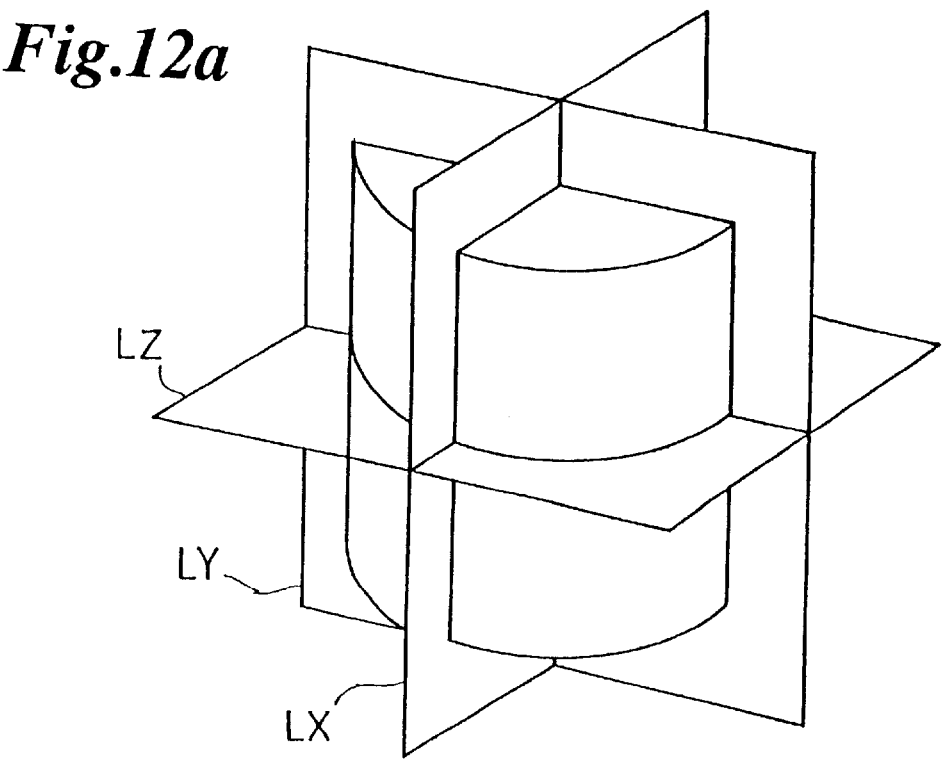
FIG. 12 is an explanatory view of an X-ray imaging target area (imaging target area index) of the X-ray object positioning apparatus for use in an X-ray imaging apparatus of the present invention.
Figure 12B:
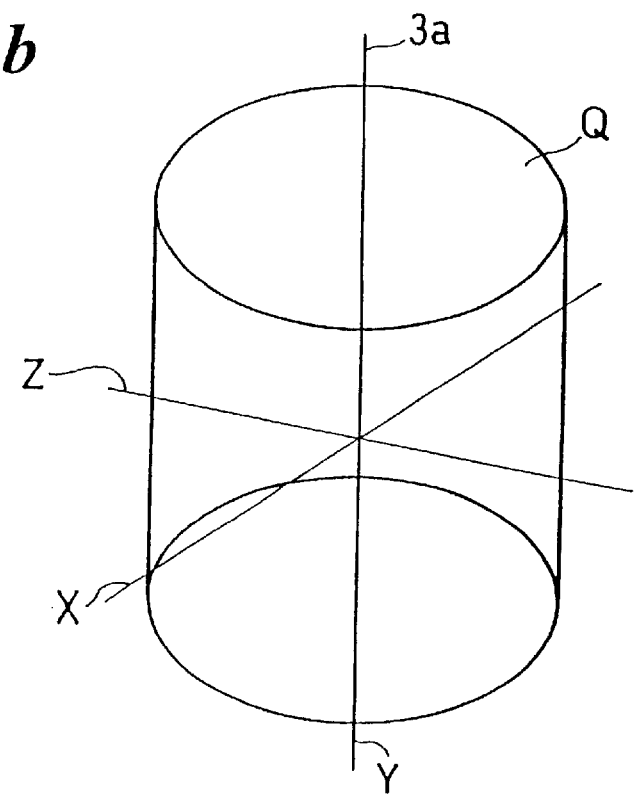
Figure 14A:
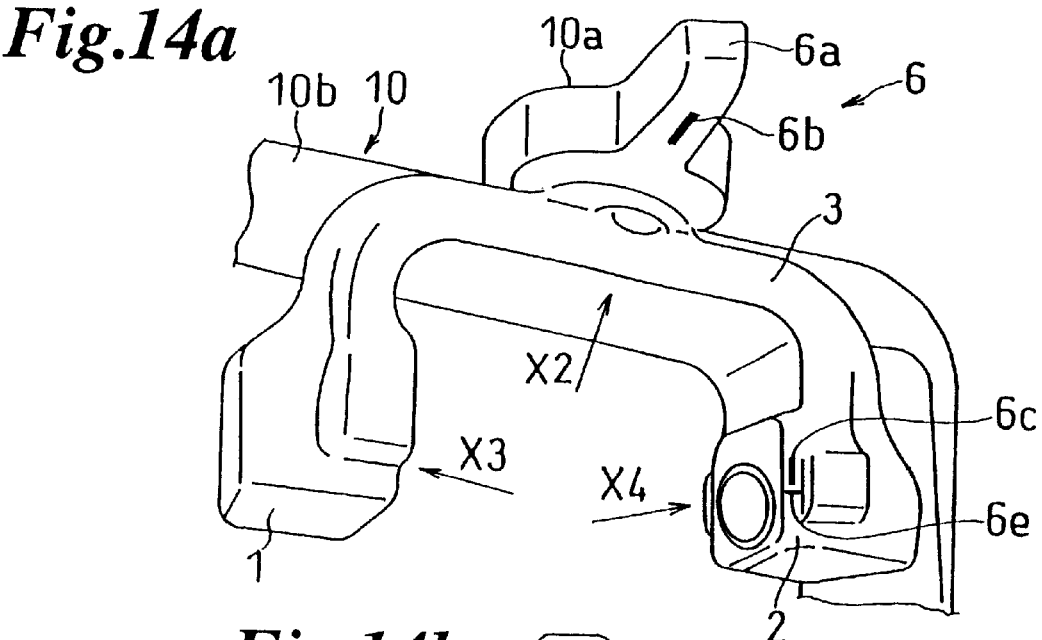
FIG. 14 is an explanatory view of guide beam generation means according to the present invention.
Figure 14B:
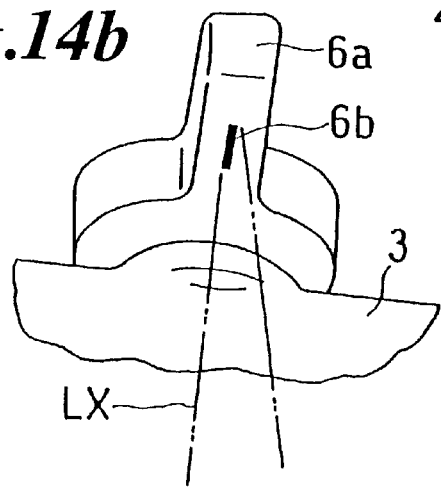
Figure 14C:
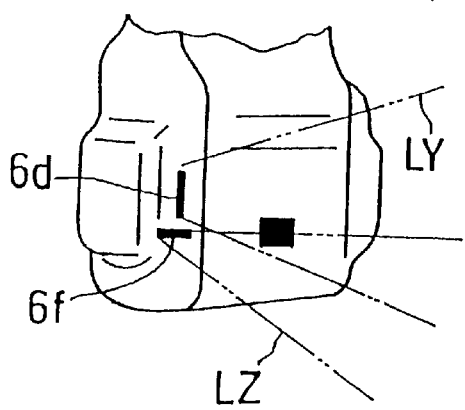
Figure 14D:
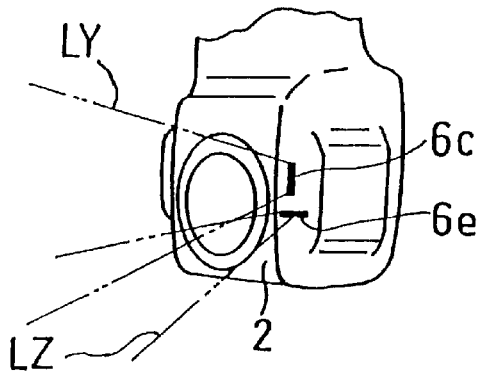

FIG. 12 is an explanatory view of an imaging target area index of an X-ray object positioning apparatus for use in an X-ray imaging apparatus of the present invention.

FIG. 12a shows relations between the imaging target area index Q and each guide beam LX, LY, LZ.

As understood by this figure, each guide beam LX, LY, LZ is a thin flat beam emitted to show the position of a crosswise direction (X direction), a lengthwise direction (Y direction) and a vertical direction (Z direction) of the imaging target area index Q. Their intersection becomes the center of the imaging target area index Q and also agrees with the rotation center 3a of the rotary arm in case of an ortho X-ray CT apparatus.

Therefore, the relation between the guide beam and the object can be easily understood by simultaneously showing the guide beams LX, LY, LZ on the display of the object model which has been explained about FIG. 1. Because of such functions, when these guide beams LX, LY, LZ are shown on the display means 7, they are called as a coordinate axis index LX, LY, LZ.

FIG. 13a is a front view of an X-ray imaging apparatus provided with an X-ray object positioning apparatus for use in an X-ray imaging apparatus of the present invention and FIG. 13b is its side view, a part of which is broken.

The X-ray object positioning apparatus for use in an X-ray imaging apparatus of the present invention can bring out its effect specifically in the ortho X-ray CT apparatus which requires positioning of the imaging target area index Q on a local area in the object body. Here an X-ray imaging apparatus 20 constructed as such an ortho X-ray CT apparatus will be explained hereinafter.

The X-ray imaging apparatus 20 has an X-ray generator 1 for radiating conical X-ray beams, a two-dimensional image sensor 2 (X-ray detector) which has a conventional construction by combining an X-ray image intensifier, for short X-ray II, and a CCD camera, a rotary arm 3 which can rotate accurately without runout around a fixed rotation center 3a, object fixing means 4 comprised of a chair 4b on base 41 having head fixing means 4a at an upper part of its back 4ba to make the object which is a patient sit on the chair, imaging position moving means 5 for moving the imaging position of conical X-ray beams radiated on the object against the X-ray imaging target area which is defined by the rotation center 3a of the rotary arm 3 and its rotating flat height, a support 6a for supporting a part of a guide beam generator which will be explained later, a display 7 for showing an object model, and a main frame 10 which is a support for the entire apparatus and is a gate type rigid structure.

The imaging position moving means 5 is comprised of crosswise moving means 51 for moving the object fixing means 4 in crosswise from side to side, lengthwise moving means 52 for moving it back and forth, vertical moving means 53 for moving it up and down, and further tilting means 54 for inclining the object against a radiating horizontal direction of conical X-ray beams. The imaging position moving means 5 constructs X-ray imaging position setting means 8 together with the object fixing means 4, the display 7 and guide beam generation means 6, will be explained later.

The display 7 is provided for an operation panel 10e positioned in such a manner that an operator can easily operate on a surface of one vertical beam 10c on the main frame 10, which will be detailed later, while standing. The display 7 shows an object model diagram and becomes an operational guide display of the entire apparatus.

The operation panel 10e has a movement switch for moving the chair 4b on which the object sits in crosswise, lengthwise and vertical direction. The object O which is fixed on the object fixing means 4 is moved by operating the movement switch after calibration. The moving condition is displayed on the display 7 interlocking with the movement of the imaging target area index Q against the object model OM as shown in FIG. 1.

The object fixing means 4 may be moved interlocking with the movement of the position of the imaging target area index Q against the object model OM shown on the display 7 by operating an operation switch of the operation panel 10e.

The main frame 10 has an arm 10a for rotatably supporting the rotary arm 3 suspending the X-ray generator 1 and the two-dimensional X-ray imaging sensor 2 in opposed condition, a pair of lateral beams 10b securely supporting a base end of the arm 10a, a pair of vertical beams 10c supporting the lateral beam 10b and a base 10d on which a pair of vertical beams 10c are securely placed and which is a base of the entire apparatus 20.

A highly rigid steel material is used for the members of the main frame 10 and braces and angular reinforcing members are appropriately used for resisting deformation and so as not to vary the rotation center 3a of the rotary arm 3 during rotation.

The main frame 10 is constructed not to cause rotary deflection of the rotary arm 3, thereby it is applicable for the ortho X-ray CT apparatus which requires no rotary deflection.

According to such a construction, the X-ray imaging apparatus 20 can execute ortho X-ray CT in good condition and further the X-ray imaging target area can be positioned at a desirable position in the object body by the X-ray imaging position setting means 8.

In this embodiment, the object is moved while securing the rotation center 3a of the rotary arm 3 which is a standard of the X-ray imaging target area, contrary, the rotating center 3a of the rotary arm 3 may be moved without moving the object.

FIG. 14 is an explanatory view of guide beam generation means according to the present invention. FIG. 14a is a fragmentary view in the direction of the arrow X1 of FIG. 13, FIG. 14b is a fragmentary view in the direction of the arrow X2 of FIG. 14a, FIG. 14c is a fragmentary view in the direction of the arrow X3 of FIG. 14a and FIG. 14d is a fragmentary view in the direction of the arrow X4 of FIG. 14a.

The guide beam generation means 6 has a support 6a extended from the arm 10a, crosswise guide beam generation means 6b provided for the support 6a for radiating crosswise guide beams LX, a pair of lengthwise guide beam generation means 6c, 6d provided for the X-ray generator 1 and the two-dimensional X-ray image sensor 2 respectively for radiating lengthwise guide beams LY, and vertical guide beams generation means 6e, 6f provided for the X-ray generator 1 and the two-dimensional X-ray image sensor 2 respectively for radiating vertical guide beams LZ.

According to such a construction, guide beams LX, LY, LZ can be irradiated on the object body as shown in FIG. 11 and the guide beam generation means 6 can be functioned as calibration means of the present invention.

The reason why the beam generation means are provided in a pair from side to side for the crosswise guide beam LY and the vertical guide beam LZ is that guide beams can be seen from an irradiating side but cannot be seen from the other side blocked by the object if only one beam generation means is provided. Therefore, a pair of guide beam generation means 6c and 6d, 6e and 6f are constructed in such a manner that irradiating guide beams are opposed.

If such constructed guide beams are used, calibration can be executed without touching the object and further the guide beam itself becomes a guide for showing the X-ray imaging target area on the object surface so that the target area can be easily comprehended.

Figure 15:
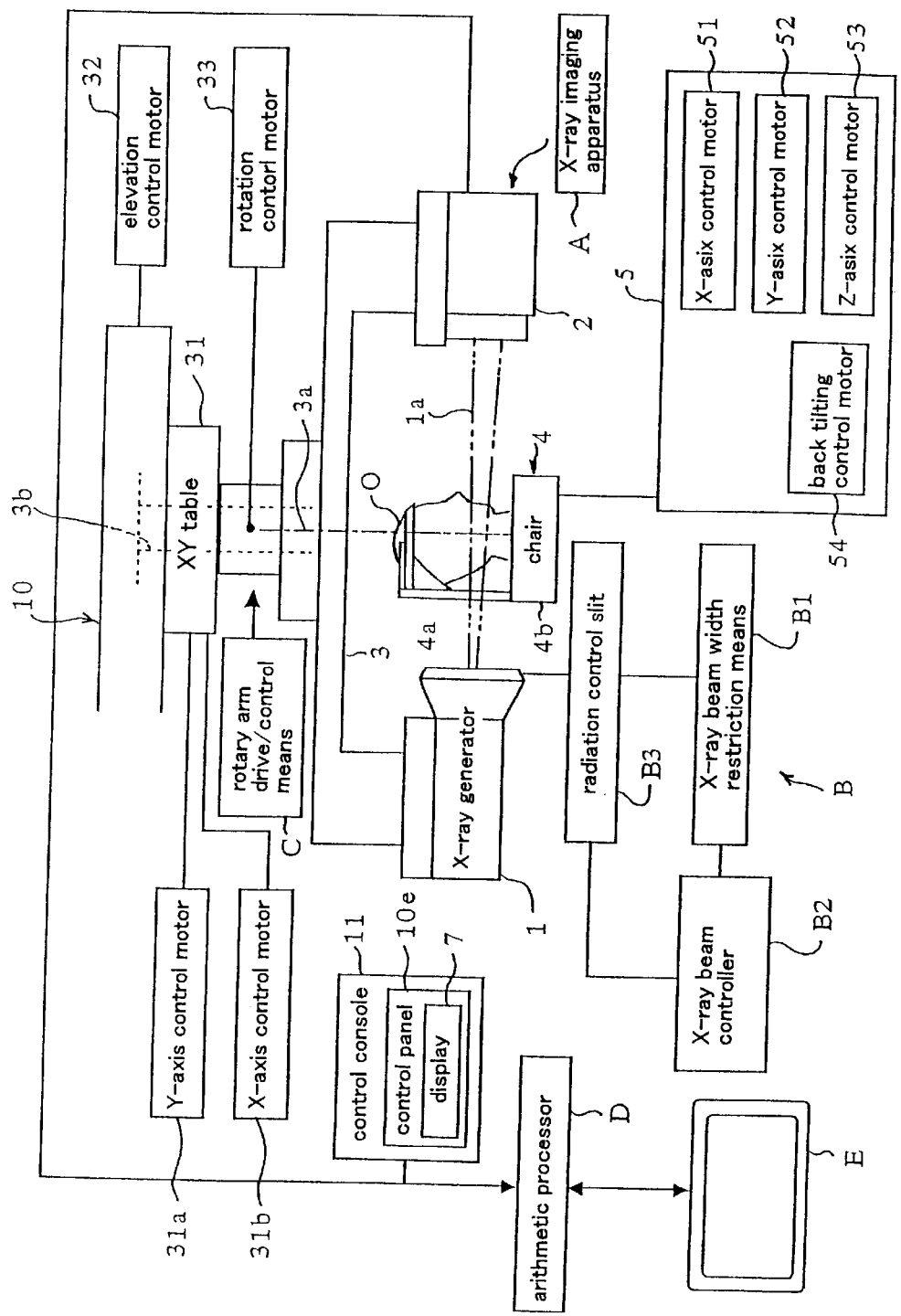
FIG. 15 is a basic construction showing the inside of the X-ray imaging apparatus of FIG. 5.

FIG. 15 is a basic construction showing the inside of the X-ray imaging apparatus of FIG. 13.

The ortho X-ray CT apparatus 20 has X-ray imaging means A, X-ray beam control means B, rotary arm driving control means C, arithmetical processing means D, a display monitor E, object holding means 4, a main frame 10, an operation console 11 and an operation panel 10e.

The X-ray imaging means A has a rotary arm 3, which suspends an X-ray generator 1 and a two-dimensional imaging sensor 2 opposing each other.

The X-ray beam control means B provided for the X-ray generator 1 has X-ray beam width restriction means B1, an X-ray beam controller B2, and an irradiation control slit B3. X-ray beams irradiated from an X-ray tube are controlled by the X-ray beam width restriction means B1 in order to radiate conical X-ray beams 1a with a desirable beam width.

The two-dimensional X-ray image sensor 2 is constructed such that X-rays run into a scintillator layer provided on the surface of the X-ray II is changed to a visible light, the visible light is converted to electrons by a photoelectric converter and is electrically intensified, and the electrons are changed to visible light by a fluorescent material to be pictured by a two-dimensionally arranged CCD (charge coupled device) camera through a lens.

An X-ray image sensor such as a cadmium telluride detector and a well known X-ray image sensor such as a CCD image sensor which is a combination of a scintillator, a glass fiber and the CCD can be used as an image sensor.

The rotary arm 3 is provided with an XY table 31, an elevation control motor 32 and a rotation control motor 33. When an X-axis control motor 31b and a Y-axis control motor 31a are controlled, the rotation center 3a of the rotary arm 3 can be adjusted in an XY direction. The center 3a is elevated up and down by driving the elevation control motor 32. In case of picturing, the rotation control motor 33 is driven at a uniform velocity so that the rotary arm 3 is designed to be rotated around the object O. The elevation control motor 32 comprises vertical position control means of the rotary arm 3.

The rotation center 3a of the rotary arm 3, that is a rotary axis, is provided vertically, the rotary arm 3 is rotated vertically and conical X-ray beams 1a are locally and horizontally irradiated, thereby achieving a vertical type apparatus which can be installed on a small space.

The rotation control motor 33 comprises rotary drive means of the rotary arm 3, uses a motor such as a servo motor which can control its rotational speed and rotational position freely, and is directly and axially attached to the rotary center 3a of the rotary arm 3.

Accordingly, the rotary arm 3 can be rotated at a uniform velocity or a variable velocity and its rotational position can be known along a time axis so that it is available for taking out X-ray transmitted images by the two-dimensional image sensor 2 in exact timing and further an ortho X-ray CT without runout can be effectively executed.

A hollow part 3b is provided for the rotation center 3a of the rotary arm 3. It is required to make a hollow part for all the members provided on the rotation center 3a in order to have such a hollow part 3b. For this purpose, a servo motor with a hollow axis can be used as a rotation control motor 33.

The hollow part 3b is provided to arrange a connection wire between the X-ray generator and the two-dimensional X-ray image sensor 2 suspended from the rotary arm 3 and the operation console 11 of the main frame 10.

The method for arranging the wire becomes a problem in order to provide an electric wring for rotating members. If the connection wire is thus arranged through the rotation center 3a of the rotary arm 3, affection caused by rotation such as twist can be minimized and a preferable effect such as a beautiful appearance can be obtained.

Rotary means C is comprised of a combination of the position control means 31 such as an XY table in this embodiment, the elevation control motor 32 and the rotation control motor 33, however the present invention isn't limited to such construction. As the most easiest construction, the center 3a of the rotary arm 3 may be manually operated by a handle so as to position appropriately.

In this figure, the imaging position moving means 5 for moving the object fixing means 4 as explained in FIG. 13 is more specifically shown as an X-axis control motor of the crosswise moving means 51, a Y-axis control motor of the lengthwise moving means 52, a Z-axis control motor of the vertical moving means 53 and a back tilting control motor 54 as tilting means.

X-axis, Y-axis and Z-axis lineal moving table (not shown) driven by these motors 51-54 are comprised of well-known cross roller guides and a combination of typical bearing and guide, thereby enabling a linear movement. The movement of the linear moving table on the X-axis, Y-axis and Z-axis can be executed by applying a rack-and-pinion system, a ball screw system and a general screw axis. Any one of them which can most accurately position is preferable.

Accordingly, the head of the object O sitting on the chair 4b is secured by the head fixing means 4a and the imaging target area index Q in the object O can be positioned to accord with the rotation center 3a of the rotary arm 3 by means of the imaging position moving means 5. On the other hand, the imaging target area index Q in the object body O may be agreed with the rotation center 3a of the rotary arm 3 by moving the rotary arm 3 by means of the XY table 31 and the elevation control motor 32 instead of moving the object fixing means 4 by the imaging position moving means 5.

The apparatus 20 has both the imaging position moving means 5 for moving the object and the XY table 31 and the elevation control means 32 for moving the rotary arm 3 which is an irradiating side in order to positioning the rotation center 3a, namely positioning for X-ray imaging. However only one of them may be provided. In case of ortho X-ray CT, it is important not to cause runout of the rotation center 3a so that it is preferable to rotate only the rotary arm 3 and the rotation center 3a is secured.

Thus, positioning suitable for imaging can be done while the object is sitting on the chair, achieving an apparatus which is gentle for the object.

Arithmetic processing means D includes a processor operable at high speed for image processing and analysis. A predetermined processing is executed after the X-ray transmission image produced on the two-dimensional image sensor 2 is preprocessed so that a three-dimensional X-ray absorption coefficient data in the object through which X-rays are transmitted is calculated. Furthermore, computation such as projection of the data on a projection surface is executed, then the projection image or a panoramic X-ray image is shown on the external display means E and is stored in a required storage means as an image information.

Figure 16:
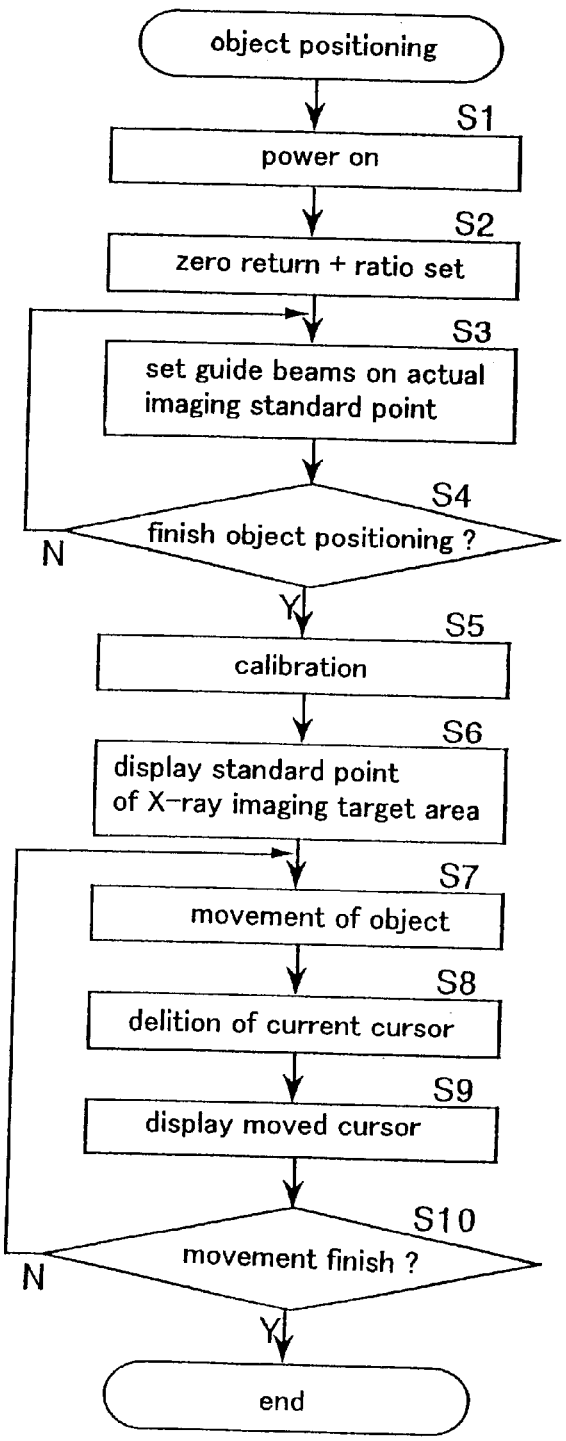
FIG. 16 is a flow chart showing object positioning procedures according to the X-ray object positioning apparatus for use in an X-ray imaging apparatus of the present invention.

FIG. 16 is a flow chart showing object positioning procedures according to the X-ray object positioning apparatus for use in an X-ray imaging apparatus of the present invention.

Procedures of calibration and object positioning method explained referring to FIG. 1 will be explained according to this flow chart.

When power is turned on (S1), zero return is executed in each direction (for example X-axis). Then the object size is selected, whereby the ratio between moving amount of the imaging position moving means 5 and that of the imaging target area index Q on the display 7 is determined, and the displayed size of the imaging target area index Q on the display 7 is determined correspondingly (S2).

The object fixing means 4 is then moved by the imaging position moving means 5, and irradiated guide beams LX, LY, LA are arranged so as to irradiate the actual imaging standard point P of the object (S3), thus repeating such operations until all the guide beams are arranged (S4).

After completing such positioning, calibration is executed such that the actual imaging standard point P of the object and the imaging standard point PM of the object model are agreed (S5). In other words, the position of the imaging target area index Q on the object model is moved at the same distance as the object's movement so that the position of the imaging target area index Q is designed to become the imaging standard point PM of the object model corresponding to the moved amount.

Thus the imaging target area index Q is shown on the imaging standard point PM on the object model (S6) (shown with dotted lines in FIG. 1), the imaging position moving means 5 is activated so as to move toward the tooth 7 which is an imaging target, thereby moving the object (S7).

Corresponding to this movement, the display deletes the present cursors, namely displays of the imaging target area index Q and the guide beams LX, LY (S8) and shows thus moved cursors corresponding to the moved positions (S9), thereby repeating these operations till completion of movement (S10).

After completing such movement, procedures for positioning the object are finished.

Figure 17:
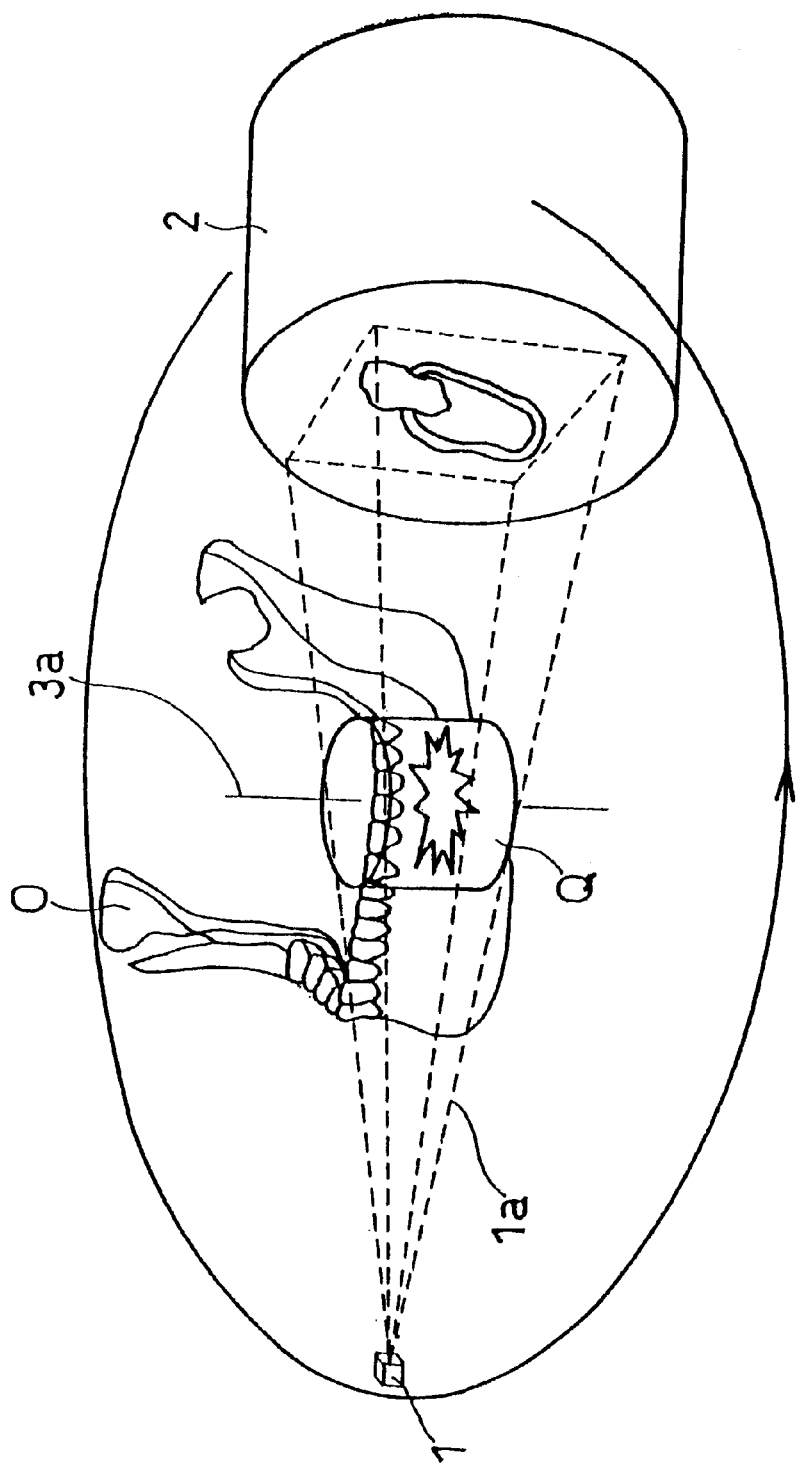
FIG. 17 is a conceptual diagram of X-ray imaging of the X-ray computed tomography apparatus of the present invention.

FIG. 17 is a conceptual diagram of X-ray imaging of the ortho X-ray computed tomography apparatus of the present invention.

The X-ray imaging position setting means of the present invention is preferably used for locally irradiating X-rays on a part of the object. The imaging concept of the ortho X-ray CT apparatus, which is a most suitable application, will be explained.

According to the apparatus, conical X-ray beams are locally radiated on a local region of the object O while rotating a rotary arm suspending an X-ray generator 1 and a two-dimensional X-ray image sensor 2 facing each other, namely so as to cover the local region with the imaging target area index Q. The picturing conditions for this purpose are that conical X-ray beams 1a covering only the local region to be pictured are radiated from the X-ray generator 1 and the rotary arm 3 is driven to be rotated while fixing a rotation center 3a on the center of the local region to be pictured.

The electrical signals on the two-dimensional X-ray imaging sensor 2 obtained by thus radiating are digitalized and backprojected so as to obtain a three-dimensional X-ray absorption coefficient of the irradiated local region, thereby obtaining optional sectional images of the local region. Further according to this, the exposed dose of X-rays can be reduced to a few tenths or a few hundredths compared to the prior art which radiates X-rays on the entire object.

This imaging method is based on an idea that the projection data of the local region on which conical X-ray beams 1a are locally radiated, namely the imaging target area index Q, is always obtained, but the conical X-ray beams temporally transmit the other area surrounding the local region according to rotation compared to the local region and there is only a minute affection on the projected data, so that the affection on the projection data other than the local region can be almost ignored in case of backprojection.

If the X-ray absorption coefficient difference between the local region to be pictured and its surrounding area is large, namely there are teeth, bones and implants in the local regions, and such shapes are diagnosed, the obtained sectional images can have enough contrast so that such images are applicable for actual diagnosis only by analyzing the pictured images obtained by locally radiating conical X-ray beams only on the local region.

The X-ray object positioning apparatus of the present invention is suitable for positioning in case of local radiation which is considered to be most important for such an ortho X-ray CT apparatus, thereby achieving both effects interactively.

What is claimed is:

1. An X-ray object positioning apparatus for use in X-ray imaging apparatus which irradiates X-rays an object to be examined to produce an X-ray absorption coefficient of a desired region of the object by means of X-rays transmitted through the object, the X-ray object positioning apparatus comprising:
    object fixing means for fixing and holding said object;
    imaging position moving means for relatively moving an X-ray imaging target area relative to the fixed object on said object fixing means; and
    display means for variably showing the relative positional relation between an object model corresponding to said object and an imaging target area index corresponding to said X-ray imaging target area;
    whereby the position between said object and said X-ray imaging target area is set by the moving operation for the position between said object model and said imaging target area index on said display means, in a manner that the relative positional relation between said object model and said X-ray imaging target area index, both displayed on said display means, conforms with the relative positional relation between said object and said X-ray imaging target area, moved by said imaging position moving means.

2. The X-ray object positioning apparatus for use in X-ray imaging apparatus as set forth in claim 1, wherein in case that the position between said object model and said imaging target area index is set on said display means, said object model is moved while said imaging target area index not moved.

3. The X-ray object positioning apparatus for use in X-ray imaging apparatus as set forth in claim 1, wherein in case that the position between said object model and said imaging target area index is set on said display means, said imaging target area index is moved while said object model not moved.

4. The X-ray object positioning apparatus for use in an X-ray imaging apparatus as set forth in claim 1, wherein in case that the position between said object model and said imaging target area index is set on said display means, the relative moving relation between said object model and said imaging target area index is varied in accordance with the relative moving relation between said object fixed on said object fixing means and said X-ray imaging target area.

5. The X-ray object positioning apparatus for use in an X-ray imaging apparatus as set forth in claim 1, further comprising calibration means for according an actual imaging standard point provided on said object fixed on said object fixing means and a model imaging standard point of the object model previously prepared according to said object,
    wherein the position between said object model and said imaging target area index is set after according said actual imaging standard point with said model imaging standard point by means of said calibration means.

6. The X-ray object positioning apparatus for use in an X-ray imaging apparatus as set forth in claim 5, further comprising guide beam generation means for emitting guide beams which functions as said calibration means.

7. The X-ray object positioning apparatus for use in an X-ray imaging apparatus as set forth in claim 1, wherein said display means is constructed such that said object model appears thereon by a fixed size despite of said object size and such that the size of said imaging target area index appears thereon in inverse proportion to said object size.

8. The X-ray object positioning apparatus for use in an X-ray imaging apparatus as set forth in claim 1, wherein said display means is constructed such that said imaging target area index appears thereon by a fixed size despite of said object size and such that the size of said object model appears thereon in proportion to said object size.

9. The X-ray object positioning apparatus for use in an X-ray imaging apparatus as set forth in claim 1, wherein said display means is constructed such that a coordinate axis index which defines a central position of said imaging target area index further appears thereon.

10. The X-ray object positioning apparatus for use in an X-ray imaging apparatus as set forth in claim 9, wherein said imaging position moving means further comprises coordinate axis rotation means for rotating said coordinate axis defining a central position of said X-ray imaging target area against an imaging standard coordinate system.

11. The X-ray object positioning apparatus for use in an X-ray imaging apparatus as set forth in claim 1, wherein said object is a dental jaw bone.

12. The X-ray object positioning apparatus for use in an X-ray imaging apparatus as set forth in claim 1, wherein said X-ray imaging apparatus is a local X-ray radiation computed tomography apparatus, wherein said object is a dental jaw bone, and wherein said X-ray imaging target area is defined as a cylindrical area of which center is a rotation center of X-rays in case of said local X-ray radiation computed tomography, where conical X-ray beams are irradiated all the time during X-ray radiation computed tomography.

13. The X-ray object positioning apparatus for use in an X-ray imaging apparatus as set forth in claim 12, wherein the position of said X-ray imaging target area is settable toward a lower jaw and an upper jaw of said dental jaw bone.

14. An X-ray imaging apparatus provided with the X-ray object positioning means according to any one of claims 1–13.

15. The X-ray imaging apparatus as set forth in claim 14, wherein said X-ray imaging apparatus is a local X-ray radiation computed tomography apparatus.

* * * * *